US006015891A

United States Patent [19]
Adang et al.

[11] Patent Number: 6,015,891
[45] Date of Patent: *Jan. 18, 2000

[54] SYNTHETIC INSECTICIDAL CRYSTAL PROTEIN GENE HAVING A MODIFIED FREQUENCY OF CODON USAGE

[75] Inventors: Michael J. Adang, Athens, Ga.; Elizabeth E. Murray, Madison, Wis.

[73] Assignee: Mycogen Plant Science, Inc., San Diego, Calif.

[*] Notice: This patent is subject to a terminal disclaimer.

[21] Appl. No.: 08/705,438

[22] Filed: Aug. 29, 1996

Related U.S. Application Data

[60] Division of application No. 08/369,835, Jan. 6, 1995, Pat. No. 5,567,600, which is a continuation-in-part of application No. 08/057,191, May 3, 1993, Pat. No. 5,380,831, which is a continuation of application No. 07/827,844, Jan. 28, 1992, abandoned, which is a continuation of application No. 07/242,482, Sep. 9, 1988, abandoned.

[51] Int. Cl.[7] ............................ C12N 15/00; C12N 15/32; C12N 15/82
[52] U.S. Cl. ..................... 536/23.71; 435/440; 435/468
[58] Field of Search ..................... 536/23.71; 435/172.3, 435/320.1, 69.1, 419, 468, 440; 800/205, 279, 302

[56] References Cited

U.S. PATENT DOCUMENTS

| | | | |
|---|---|---|---|
| 4,356,270 | 10/1982 | Itakura | 435/317 |
| 4,888,282 | 12/1989 | Beremand et al. | 435/193 |
| 5,254,799 | 10/1993 | De Greve | 800/205 |
| 5,276,268 | 1/1994 | Strauch et al. | 800/205 |
| 5,380,831 | 1/1995 | Adang et al. | 536/23.71 |
| 5,567,600 | 10/1996 | Adang et al. | 536/23.71 |

FOREIGN PATENT DOCUMENTS 0305275   3/1989   European Pat. Off. .

OTHER PUBLICATIONS

Sekar, V. et al. (1987) "Molecular cloning and characterization of the insecticidal crystal protein gene of *Bacillus thuringiensis* var. tenebrionis" Pro. Natl. Acad. Sci. USA 84:7036–7040.
McPherson, S. A. et al. (1988) "Characterization of the Colopteran–specific protein gene of *Bacillus thuringiensis* var. Tenebrionis" Biotechnology 6(1):61–6.
Vaeck, M. et al. (1987) "Transgenic Plants protected from insect attach" Nature 328:33–37.
Murray, E. E. et al. (1989) "Codon usage in plant genes" Nucleic Acids Research 17(2):477–498.
Perlak, F. J. et al. (1991) "Modification of the coding sequence enhances plant expression of insect control protein genes" Proc. Natl. Acad. Sci. USA 88:3324–3328.
Hernastadt et al. (1986) Biotechnology 4:305–308.
Sekar et al. (1987) Proc. Natl. Acad. Sci. 84:7036–7040.
McPherson et al. (1988) Biotechnology 6:61–66.

Vaeck et al. (1987) Nature 328:33–37.
Barton et al. (1987) Plant Physiol. 85: 1103–1109.
Hofte et al. (1988) FEBS Lett. 226:364–370.
Bennetzen and Hall (1982) J. Biol. Chem. 257:3026–3031.
Hoekema et al. (1987) Mol. Cell. Biol. 7:2914–2924.
Boudraa (1987) Genet. Sel. Evol. 19:143–154.
Grantham et al. (1986) Oxford Surveys in Evol. Biol. 3:48–81.
Taylor et al. (1987) Mol. Gen. Genet. 210:572–577.
Joshi (1987) Nucl. Acids Res. 15:9627–9640.
Vankan and Fillipowicz (1988) Embo J. 7:791–799.
Tuerk et al. (1988) Proc. Natl. Acad. Sci. 85:1364–1368.
Krieg et al. (1983) Z. Angew. Entomol. 96:500–508.
Bernahard (1986) FEMS Microbiol. Lett. 33:261–265.
Neill et al. (1987) Gene 55:303–317.
Rothstein et al. (1987) Gene 55:353–356.
Coraggio et al. (1986) EMBO J. 5:459–465.
Fuzakawa et al. (1987) FEBS Lett. 224:125–127.
Vies et al. (1986) EMBO J. 5:2439–2444.
Gatenby et al. (1987) Eur. J. Biochem. 168:227–231.
Viotti et al. (1978) Biochim. Biophys. Acta 517:125–132.
Hames and Higgins (eds) (1985) *Nucleic Acid Hybridisation*, IRL Press, Oxford, UKe.
Caruthers, M. (1983) In Methodology of DNA and RNA Sequencing, Chapter 1, Weissman (ed.), Praeger Publishers, New Yor.I.
Lo et al. (1984) Proc. Natl. Acad. Sci. 81:2285–2289.
Grantham et al. (1985) Bull. inst. Pasteur 83:95–148.
Matsuoka et al. (1987) J. Biochem. 102:673–676.
Mandecki et al. (1985) Proc. Natl. Acad. Sci. 82:3543–3547.
Feretti et al. (1986) Proc. Natl. Acad. Sci. 83:599–603.
Paszkowski, J. et al. (1984) EMBO J. 3: 2717.
Fromm, M. et al. (1985) Proc. Natl. Acad. Sci. USA 82:5824.
Crossway, A. et al. (1986) Mol. Gen. Genet. 202:179.
Hooykaas–Van Slogteren, G. et al. (1984) Nature 311:763.
Dandekar, A. et al. (1987) Biotechnology 5:587.
An, G. et al. (1985) EMBO J. 4:277.
Herrera–Estrella, L. et al. (1983) Nature 303:209E.
Herrera–Estrella, L. et al. (1983) EMBO J. 2:987.
Herrera–Estrella, L. et al. (1985) in Plant Genetic Engineering, Cambridge University Press, New York, p. 63.
asadaban, M. J. and Cohen, S.N. (1980) J. Mol. Biol. 138:179–207.
Marsh, J. L. et al. (1984) Gene 32:481–485.
Kronstad et al. (1983) J. Bacteriol. 154: 419–428.
Adang et al. (1987) in *Biotechnology in Invertebrate Pathology and Cell Culture*, K. Maramorosh (ed.) Academic Press, Inc. New York, pp 85–99.

(List continued on next page.)

*Primary Examiner*—Lynette R. F. Smith
*Assistant Examiner*—Amy J. Nelson
*Attorney, Agent, or Firm*—Saliwanchik, Lloyd & Saliwanchik

[57] ABSTRACT

Synthetic *Baccilus thuringiensis* toxin genes designed to be expressed in plants at a level higher than naturally-occurring *Bt* genes are provided. These genes utilize codons preferred in highly expressed monocot or dicot proteins.

6 Claims, 5 Drawing Sheets

OTHER PUBLICATIONS

Schnepf and Whitteley (1985) J. Biol. Chem 260:6273–6280.
Pfitzinger et al. (1987) Nucl. Acids Res. 15: 1377–1386.
Sharp and Li (1986) Nucl. Acids Res. 14:7734–7749.
Matteucci et al. (1981) J. Am. Chem. Soc. 103:3185–3192.
Beaucage et al. (1981) tetrahedron Lett. 22: 1859–1862.
McBride et al. (1988) Biotechniques 6:362–367.
Maniatis (1982) *Cloning Manual*, Fritsch and Sambrook (eds.), Cold Spring Harbor Laboratory, Cold Spring Harebor, New York.

Sanger et al. (1977) proc. Natl. Acad. Sci. 74:5463–5467.
Russell and Bennett (1982) Gene 20: 231–244.
Yanisch–Perron, C. et al. (1985) Gene 33: 103–119.
Barnes (1986) J. Cell Biochem . O (10 part C) 47.
Boswell et al. in *Computational Molecular Biology, Sources and Methods for Sequence Analysis*(Leak, ed.) Oxford University Press, Oxford, 1986, pp. 170–171.
Schnepf HE. "*Bacillus thuringiensis* toxins: Regulation, activities and structural diversity." Current Opinion Biotech. 6: 305–312, 1995.

FIG.1A

```
                                                          G  A                                  A   A
        CACTATTCCATTGTATGATGTTCGACTCTACCCAAAGGAGGTTAAAACCGAATTGACTAGAGACGTTTTAACCGATCCATTGTCGGAGTCAACAACCT
701     ---------+---------+---------+---------+---------+---------+---------+---------+---------+---------+  800
         L  F  P  L  Y  D  V  R  L  Y  P  K  E  V  K  T  E  L  T  R  D  V  L  T  D  P  I  V  G  V  N  N  L

T  G                            T                    T              T                       A
        CAGAGGCTACGGAACAACCTTCTCTAACATAGAAAACTACATTCGTAAACCACATCTATTCGACTATCTGCACAGAATTCAGTTTCACACGCGGTTCCAA
801     ---------+---------+---------+---------+---------+---------+---------+---------+---------+---------+  900
         R  G  Y  G  T  T  F  S  N  I  E  N  Y  I  R  K  P  H  L  F  D  Y  L  H  R  I  Q  F  H  T  R  F  Q

T                                                                    A           T  A
        CCAGGATACTATGGAAATGACTCTTTCAACTATTGGTCCGGTAATTATGTTTCAACTAGACCAGCATAGGATCTAATGACATCATCACCTCTCCATTCT
901     ---------+---------+---------+---------+---------+---------+---------+---------+---------+---------+  1000
         P  G  Y  Y  G  N  D  S  F  N  Y  W  S  G  N  Y  V  S  T  R  P  S  I  G  S  N  D  I  I  T  S  P  F  Y

T  T  A   AGT  A                       T  A  A                   A     G
        ACGGAAACAAGTCCTCCGAGCCTGTGCAAAACTTGGAGTTTAATGGAGAGAAAGTCTATAGAGCCGTGGCCAATACCAATCTTGCCGTCTGGCCGTCCGC
1001    ---------+---------+---------+---------+---------+---------+---------+---------+---------+---------+  1100
         G  N  K  S  S  E  P  V  Q  N  L  E  F  N  G  E  K  V  Y  R  A  V  A  N  T  N  L  A  V  W  P  S  A

A  T                    T                              A                         A  A
        TGTGTACTCAGGTGTTACCAAAGTGGAATTCAGCCAATACAATGATCAGACAGATGAAGCAAGTACTCAAACTTACGACTCAAAGAGGAATGTGGGCGCG
1101    ---------+---------+---------+---------+---------+---------+---------+---------+---------+---------+  1200
         V  Y  S  G  V  T  K  V  E  F  S  Q  Y  N  D  Q  T  D  E  A  S  T  Q  T  Y  D  S  K  R  N  V  G  A

TG                                A                     T  A
        GTCAGCTGGGATTCTATCGATCAACTCCCTCCAGAAACCACCGATGAACCTCTAGAGAAGGGTTATAGCCATCAACTCAATTACGTAATGTGCTTTCTCA
1201    ---------+---------+---------+---------+---------+---------+---------+---------+---------+---------+  1300
         V  S  W  D  S  I  D  Q  L  P  P  E  T  T  D  E  P  L  E  K  G  Y  S  H  Q  L  N  Y  V  M  C  F  L  M
```

SYNTHETIC INSECTICIDAL CRYSTAL PROTEIN GENE HAVING A MODIFIED FREQUENCY OF CODON USAGE

CROSS REFERENCES TO RELATED APPLICATIONS

This is a division of application Ser. No. 08/369,835, filed Jan. 6, 1995, issued as U.S. Pat. No. 5,567,600, which is a continuation-in-part of application Ser. No. 08/057,191, filed May 3, 1993 issued as U.S. Pat. No. 5,380,831, which is a continuation of application Ser. No. 07/827,844, filed Jan. 28, 1992, now abandoned; which is a continuation of application Ser. No. 07/242,482, filed Sep. 9, 1988, now abandoned, all of which are incorporated herein by reference.

FIELD OF THE INVENTION

This invention relates to the field of bacterial molecular biology and, in particular, to genetic engineering by recombinant technology for the purpose of protecting plants from insect pests. Disclosed herein ar ethe chemical synthesis of a modified crystal protein gene from *Bacillus thuringiensis* var. *tenebrionis* (*Btt*), and the selective expression of this synthetic insecticidal gene. Also disclosed is the transfer of the cloned synthetic gene into a host microoorganism, rendering the organism capable of producing, at improved levels of expression, a protein having toxicity to insects. This invention facilitates the genetic engineering of bacteria and plants to attain desired expression levels of novel toxins having agronomic value.

BACKGROUND OF THE INVENTION

*B. thuringiensis* (*Bt*) is unique in its ability to produce, during the process of sporulation, proteinaceous, crystalline inclusions which are found to be highly toxic to several insect pests of agricultural importance. The crystal proteins of different *Bt* strains have a rather narrow host range and hence are used commercially as very selective biological insecticides. Numerous strains of *Bt* are toxic to lepidopteran and dipteran insects. Recently two subspecies (or varieties) of *Bt* have been reported to be pathogenic to coleopteran insects: var. *tenebrionis* (Krieg et al. (1983) Z. Angew. Entomol. 96:500–508) and var. *san diego* (Herrnstadt et al. (1986) Biotechnol. 4:305–308). Both strains produce flat, rectangular crystal inclusions and have a major crystal component of 64–68 kDa (Herrnstadt et al. supra; Bernhard (1986) FEMS Microbiol. Lett. 33:261–265).

Toxin genes from several subspecies of *Bt* have been cloned and the recombinant clones were found to be toxic to lepidopteran and dipteran insect larvae. The two coleopteran-active toxin genes have also been isolated and expressed. Herrnstadt et al. supra cloned a 5.8 kb BamHI fragment of *Bt* var. *san diego* DNA. The protein expressed in *E. coli* was toxic to *P. luteola* (Elm leaf beetle) and had a molecular weight of approximately 83 kDa. This 83 kDa toxin product from the var. *san diego* gene was larger than the 64 kDa crystal protein isolated from *Bt* var. *san diego* cells, suggesting that the *Bt* var. *san diego* crystal protein may be synthesized as a larger precursor molecule that is processed by *Bt* var. *san diego* but not by *E. coli* prior to being formed into a crystal.

Sekar et al. (1987) Proc. Nat. Acad. Sci. USA 84:7036–7040; U.S. patent application Ser. No. 108,285, filed Oct. 13, 1987 isolated the crystal protein gene from *Btt* and determined the nucleotide sequence. This crystal protein gene was contained on a 5.9 kb BamHI fragment (pNSBF544). A subclone containing the 3 kb HindIII fragment from pNSBF544 was constructed. This HindIII fragment contains an open reading frame (ORF) that encodes a 644-amino acid polypeptide of approximately 73 kDa. Extracts of both subclones exhibited toxicity to larvae of Colorado potato beetle (*Leptinotarsa decemlineata*, a coleopteran insect). 73- and 65-kDa peptides that cross-reacted with an antiserum against the crystal protein of var. *tenebrionis* were produced on expression in *E. coli*. Sporulating var. *tenebrionis* cells contain an immunoreactive 73-kDa peptide that corresponds to the expected product from the ORF of pNSBP544. However, isolated crystals primarily contain a 65-kDa component. When the crystal protein gene was shortened at the N-terminal region, the dominant protein product obtained was the 65-kDa peptide. A deletion derivative, p544Pst-Met5, was enzymatically derived from the 5.9 kb BamHI fragment upon removal of forty-six amino acid residues from the N-terminus. Expression of the N-terminal deletion derivative, p544Pst-Met5, resulted in the production of, almost exclusively, the 65 kDa protein. Recently, McPherson et al. (1988) Biotechnology 6:61–66 demonstrated that the *Btt* gene contains two functional translational initiation codons in the same reading frame leading to the production of both the full-length protein and an N-terminal truncated form.

Chimeric toxin genes from several strains of *Bt* have been expressed in plants. Four modified *Bt2* genes from var. *berliner* 1715, under the control of the 2' promoter of the Agrobacterium TR-DNA, were transferred into tobacco plants (Vaeck et al. (1987) Nature 328:33–37). Insecticidal levels of toxin were produced when truncated genes were expressed in transgenic plants. However, the steady state mRNA levels in the transgenic plants were so low that they could not be reliably detected in Northern blot analysis and hence were quantified using ribonuclease protection experiments. *Bt* mRNA levels in plants producing the highest level of protein corresponded to ≈0.0001% of the poly(A)$^+$ mRNA.

In the report by Vaeck et al. (1987) supra, expression of chimeric genes containing the entire coding sequence of *Bt2* were compared to those containing truncated *Bt2* genes. Additionally, some T-DNA constructs included a chimeric NPTII gene as a marker selectable in plants, whereas other constructs carried translational fusions between fragments of *Bt2* and the NPTII gene. Insecticidal levels of toxin were produced when truncated *Bt2* genes or fusion constructs were expressed in transgenic plants. Greenhouse grown plants produced ≈0.02% of the total soluble protein as the toxin, or 3 µg of toxin per g. fresh leaf tissue and, even at five-fold lower levels, showed 100% mortality in six-day feeding assays. However, no significant insecticidal activity could be obtained using the intact *Bt2* coding sequence, despite the fact that the-same promoter was used to direct its expression. Intact *Bt2* protein and RNA yields in the transgenic plant leaves were 10–50 times lower than those for the truncated *Bt2* polypeptides or fusion proteins.

Barton et al. (1987) Plant Physiol. 85:1103–1109 showed expression of a *Bt* protein in a system containing a 35S promoter, a viral (TMV) leader sequence, the *Bt* HD-1 4.5 kb gene (encoding a 645 amino acid protein followed by two proline residues) and a nopaline synthase (nos) poly(A)+ sequence. Under these conditions expression was observed for *Bt* mRNA at levels up to 47 pg/20 µg RNA and 12 ng/mg plant protein. This amount of *Bt* protein in plant tissue produced 100% mortality in two days. This level of expression still represents a low level of mRNA ($2.5 \times 10^{-4}\%$) and protein ($1.2 \times 10^{-3}\%$).

Various hybrid proteins consisting of N-terminal fragments of increasing length of the Bt2 protein fused to NPTII were produced in *E. coli* by Hofte et al. (1988) FEBS Lett. 226:364–370. Fusion proteins containing the first 607 amino acids of Bt2 exhibited insect toxicity; fusion proteins not containing this minimum N-terminal fragment were nontoxic. Appearance of NPTII activity was not dependent upon the presence of insecticidal activity; however, the conformation of the Bt2 polypeptide appeared to exert an important influence on the enzymatic activity of the fused NPTII protein. This study did suggest that the global 3-D structure of the Bt2 polypeptide is disturbed in truncated polypeptides.

A number of researchers have attempted to express plant genes in yeast (Neill et al. (1987) Gene 55:303–317; Rothstein et al. (1987) Gene 55:353–356; Coraggio et al. (1986) EMBO J. 5:459–465) and *E. coli* (Fuzakawa et al. (1987) FEBS Lett. 224:125–127; Vies et al. (1986) EMBO J. 5:2439–2444; Gatenby et al. (1987) Eur. J. Biochem. 168:227–231). In the case of wheat α-gliadin (Neill et al. (1987) supra), α-amylase (Rothstein et al. (1987) supra) genes, and maize zein genes (Coraggio et al. (1986) supra) in yeast, low levels of expression have been reported. Neill et al. have suggested that the low levels of expression of α-gliadin in yeast may be due in part to codon usage bias, since α-gliadin codons for Phe, Leu, Ser, Gly, Tyr and especially Glu do not correlate well with the abundant yeast isoacceptor tRNAs. In *E. coli* however, soybean glycinin A2 (Fuzakawa et al. (1987) supra) and wheat RuBPC SSU (Vies et al. (1986) supra; Gatenby et al. (1987) supra) are expressed adequately.

Not much is known about the makeup of tRNA populations in plants. Viotti et al. (1978) Biochim. Biophys. Acta 517:125–132 report that maize endosperm actively synthesizing zein, a storage protein rich in glutamine, leucine, and alanine, is characterized by higher levels of accepting activity for these three amino acids than are maize embryo tRNAs. This may indicate that the tRNA population of specific plant tissues may be adapted for optimum translation of highly expressed proteins such as zein. To our knowledge, no one has experimentally altered codon bias in highly expressed plant genes to determine possible effects of the protein translation in plants to check the effects on the level of expression.

SUMMARY OF THE INVENTION

It is the overall object of the present invention to provide a means for plant protection against insect damage. The invention disclosed herein comprises a chemically synthesized gene encoding an insecticidal protein which is functionally equivalent to a native insecticidal protein of Bt. This synthetic gene is designed to be expressed in plants at a level higher than a native Bt gene. It is preferred that the synthetic gene be designed to be highly expressed in plants as defined herein. Preferably, the synthetic gene is at least approximately 85% homologous to an insecticidal protein gene of Bt.

It is a particular object of this invention to provide a synthetic structural gene coding for an insecticidal protein from Btt having, for example, the nucleotide sequences presented in FIG. 1 and spanning nucleotides 1 through 1793 or spanning nucleotide 1 through 1833 with functional equivalence.

In designing synthetic Btt genes of this invention for enhanced expression in plants, the DNA sequence of the native Btt structural gene is modified in order to contain codons preferred by highly expressed plant genes, to attain an A+T content in nucleotide base composition substantially that found in plants, and also preferably to form a plant initiation sequence, and to eliminate sequences that cause destabilization, inappropriate polyadenylation, degradation and termination of RNA and to avoid sequences that constitute secondary structure hairpins and RNA splice sites. In the synthetic genes, codons used to specify a given amino acid are selected with regard to the distribution frequency of codon usage employed in highly expressed plant genes to specify that amino acid. As is appreciated by those skilled in the art, the distribution frequency of codon usage utilized in the synthetic gene is a determinant of the level of expression. Hence, the synthetic gene is designed such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG nucleotide is the least preferred codon in dicots whereas the XTA codon is avoided in both monocots and dicots. The synthetic genes of this invention also preferably have CG and TA doublet avoidance indices as defined in the Detailed Description closely approximating those of the chosen host plant. More preferably these indices deviate from that of the host by no more than about 10–15%.

Assembly of the Bt gene of this invention is performed using standard technology known to the art. The Btt structural gene designed for enhanced expression in plants of the specific embodiment is enzymatically assembled within a DNA vector from chemically synthesized oligonucleotide duplex segments. The synthetic Bt gene is then introduced into a plant host cell and expressed by means known to the art. The insecticidal protein produced upon expression of the synthetic Bt gene in plants is functionally equivalent to a native Bt crystal protein in having toxicity to the same insects.

BRIEF DESCRIPTION OF THE FIGURES

FIGS. 1A and 1B present the nucleotide sequence for the synthetic Btt gene. Where different, the native sequence as found in p544Pst-Met5 is shown above. Changes in amino acids (underlined) occur in the synthetic sequence with alanine replacing threonine at residue 2 and leucine replacing the stop at residue 596 followed by the addition of 13-amino acids at the C-terminus.

BRIEF DESCRIPTION OF THE SEQUENCES

Figure 1A:
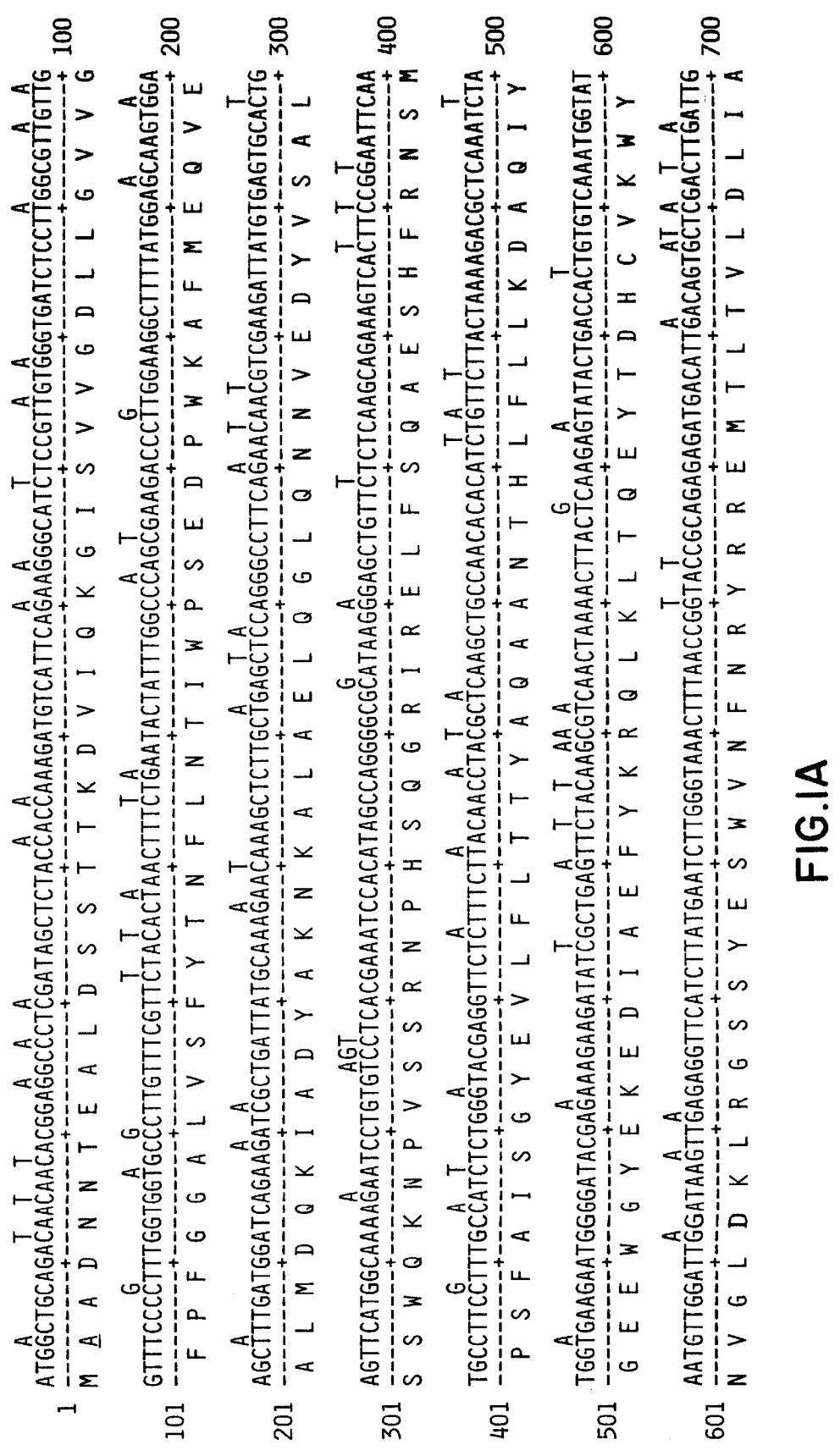
Figure 2:
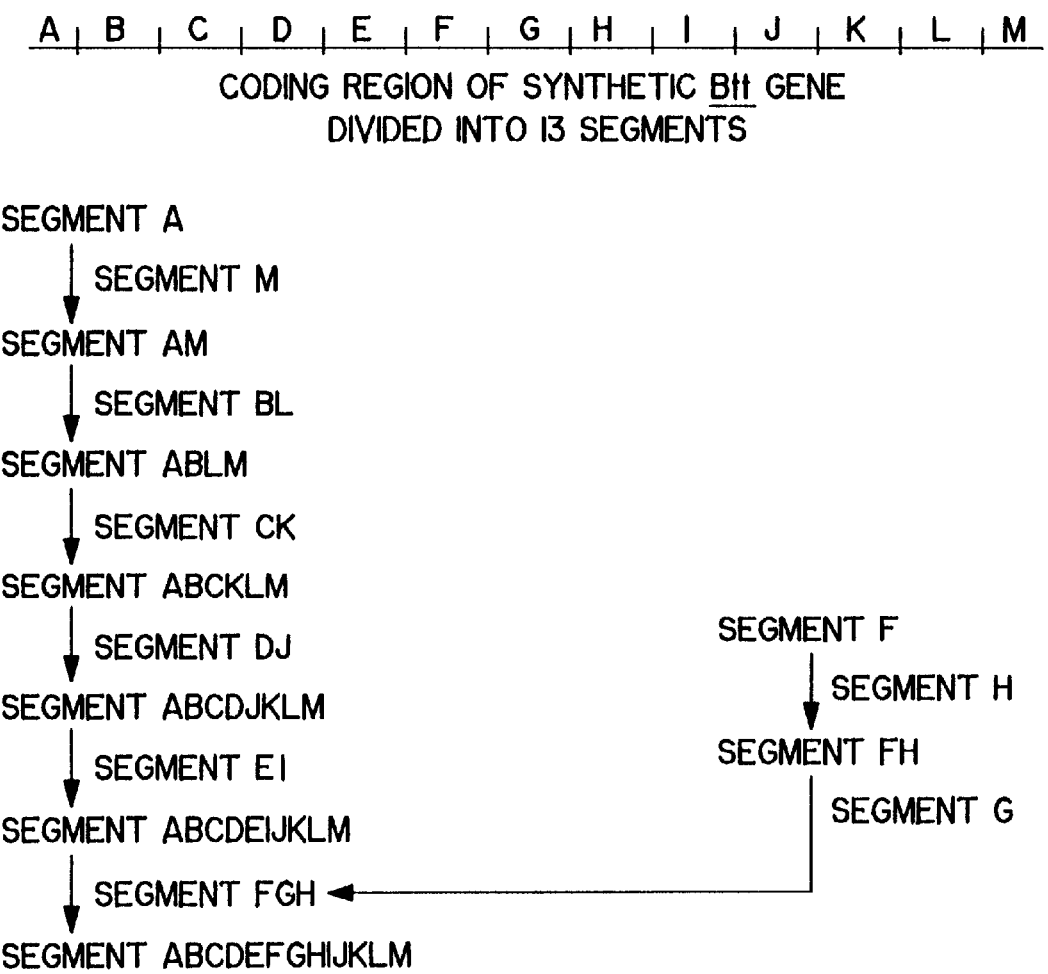
FIG. 2 represents a simplified scheme used in the construction of the synthetic Btt gene. Segments A through M represent oligonucleotide pieces annealed and ligated together to form DNA duplexes having unique splice sites to allow specific enzymatic assembly of the DNA segments to give the desired gene.

SEQ ID NO. 1 is the native DNA gene sequence corresponding to FIG. 1.

SEQ ID NO. 2 is the corresponding amino acid sequence encoded by SEQ ID NO. 1.

SEQ ID NO. 3 is the synthetic DNA gene sequence corresponding to FIG. 1.

SEQ ID NO. 4 is the corresponding amino acid sequence encoded by SEQ ID NO. 3.

SEQ ID NO. 5 is the sequence of a synthetic DNA linker described in Example 1(i).

SEQ ID NO. 6 is the sequence of the 5' plant consensus splice site found in Example 1(iii)(d).

SEQ ID NO. 7 is the sequence of the 3' plant consensus splice site found in Example 1(iii)(d).

SEQ ID NO. 8 is the nucleotide sequence of Segment A found in Table 4.

SEQ ID NO. 9 is the nucleotide sequence of Segment M found in Table 5.

DETAILED DESCRIPTION OF THE INVENTION

The following definitions are provided in order to provide clarity as to the intent or scope of their usage in the Specification and claims.

Expression refers to the transcription and translation of a structural gene to yield the encoded protein. The synthetic Bt genes of the present invention are designed to be expressed at a higher level in plants than the corresponding native Bt genes. As will be appreciated by those skilled in the art, structural gene expression levels are affected by the regulatory DNA sequences (promoter, polyadenylation sites, enhancers, etc.) employed and by the host cell in which the structural gene is expressed. Comparisons of synthetic Bt gene expression and native Bt gene expression must be made employing analogous regulatory sequences and in the same host cell. It will also be apparent that analogous means of assessing gene expression must be employed in such comparisons.

Promoter refers to the nucleotide sequences at the 5' end of a structural gene which direct the initiation of transcription. Promoter sequences are necessary, but not always sufficient, to drive the expression of a downstream gene. In prokaryotes, the promoter drives transcription by providing binding sites to RNA polymerases and other initiation and activation factors. Usually promoters drive transcription preferentially in the downstream direction, although promotional activity can be demonstrated (at a reduced level of expression) when the gene is placed upstream of the promoter. The level of transcription is. regulated by promoter sequences. Thus, in the construction of heterologous promoter/structural gene combinations, the structural gene is placed under the regulatory control of a promoter such that the expression of the gene is controlled by promoter sequences. The promoter is positioned preferentially upstream to the structural gene and at a distance from the transcription start site that approximates the distance between the promoter and the gene it controls in its natural setting. As is known in the art, some variation in this distance can be tolerated without loss of promoter function.

A gene refers to the entire DNA portion involved in the synthesis of a protein. A gene embodies the structural or coding portion which begins at the 5' end from the translational start codon (usually ATG) and extends to the stop (TAG, TGA or TAA) codon at the 3' end. It also contains a promoter region, usually located 5' or upstream to the structural gene, which initiates and regulates the expression of a structural gene. Also included in a gene are the 3' end and poly(A)+ addition sequences.

Structural gene is that portion of a gene comprising a DNA segment encoding a protein, polypeptide or a portion thereof, and excluding the 5' sequence which drives the initiation of transcription. The structural gene nay be one which is normally found in the cell or one which is not normally found in the cellular location wherein it is introduced, in which case it is termed a heterologous gene. A heterologous gene may be derived in whole or in part from any source know to the art, including a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bounded by the appropriate splice junctions. The structural gene may be a composite of segments derived from a plurality of sources, naturally occurring or synthetic. The structural gene may also encode a fusion protein.

Synthetic gene refers to a DNA sequence of a structural gene that is chemically synthesized in its entirety or for the greater part of the coding region. As exemplified herein, oligonucleotide building blocks are synthesized using procedures known to those skilled in the art and are ligated and annealed to form gene segments which are then enzymatically assembled to construct the entire gene. As is recognized by those skilled in the art, functionally and structurally equivalent genes to the synthetic genes described herein may be prepared by site-specific mutagenesis or other related methods used in the art.

Transforming refers to stably introducing a DNA segment carrying a functional gene into an organism that did not previously contain that gene.

Plant tissue includes differentiated and undifferentiated tissues of plants, including but not limited to, roots, shoots, leaves, pollen, seeds, tumor tissue and various forms of cells in culture, such as single cells, protoplasts, embryos and callus tissue. The plant tissue may be in planta or in organ, tissue or cell culture.

Plant cell as used herein includes plant cells in planta and plant cells and protoplasts in culture.

Homology refers to identity or near identity of nucleotide or amino acid sequences. As is understood in the art, nucleotide mismatches can occur at the third or wobble base in the codon without causing amino acid substitutions in the final polypeptide sequence. Also, minor nucleotide modifications (e.g., substitutions, insertions or deletions) in certain regions of the gene sequence can be tolerated and considered insignificant whenever such modifications result in changes in amino acid sequence that do not alter functionality of the final product. It has been shown that chemically synthesized copies of whole, or parts of, gene sequences can replace the corresponding regions in the natural gene without loss of gene function. Homologs of specific DNA sequences may be identified by those skilled in the art using the test of cross-hybridization of nucleic acids under conditions of stringency as is well understood in the art (as described in Hames and Higgens (eds.) (1985) *Nucleic Acid Hybridization*, IRL Press, Oxford, UK). Extent of homology is often measured in terms of percentage of identity between the sequences compared.

Functionally equivalent refers to identity or near identity of function. A synthetic gene product which is toxic to at least one of the same insect species as a natural Bt protein is considered functionally equivalent thereto. As exemplified herein, both natural and synthetic Btt genes encode 65 kDa insecticidal proteins having essentially identical amino acid sequences and having toxicity to coleopteran insects. The synthetic *Bt* genes of the present invention are not considered to be functionally equivalent to native *Bt* genes, since they are expressible at a higher level in plants than native *Bt* genes.

Frequency of preferred codon usage refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Table 1, for example, gives the frequency of codon usage for *Bt* genes, which was obtained by analysis of four *Bt* genes whose sequences are publicly available. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. Table 1, for example, gives the frequency of codon usage by highly expressed genes exhibited by dicotyledonous plants, and monocotyledonous plants. The dicot codon usage was calculated using 154 highly expressed coding sequences obtained from Genbank which are listed in Table 1. Monocot codon usage was calculated using 53 monocot nuclear gene coding sequences obtained from Genbank and listed in Table 1, located in Example 1.

When synthesizing a gene for improved expression in a host call it is desirable to design the gene such that its frequency of codon usage approaches the frequency of preferred codon usage of the host cell.

Figure 1C:
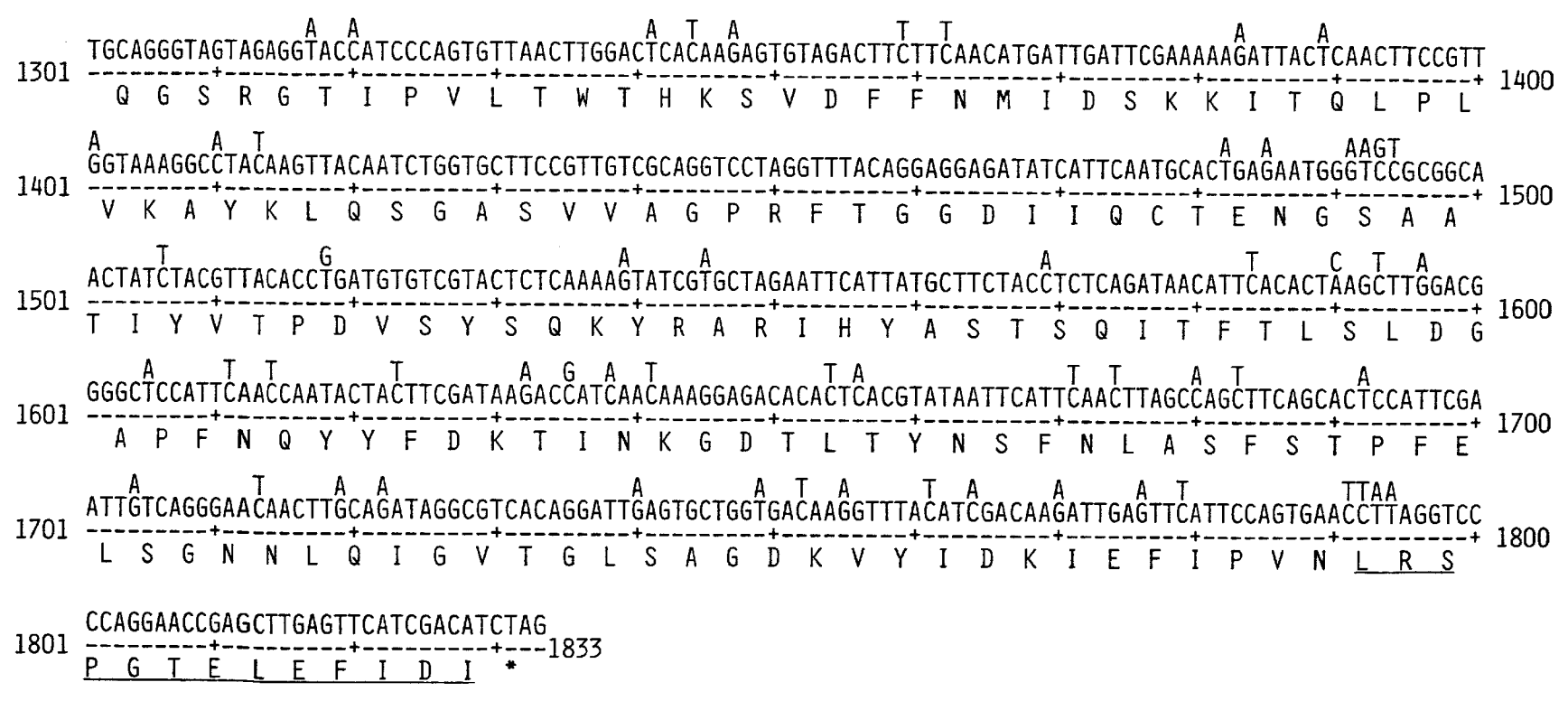

The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein this calculation includes unique codons (i.e., ATG and TGG). The frequency of preferred codon usage of the synthetic *Btt* gene, whose sequence is given in FIGS. 1A–C, is given in Table 1. The frequency of preferred usage of the codon 'GTA' for valine in the synthetic gene (0.10) deviates from that preferred by dicots (0.12) by 0.02/0.12=0.167 or 16.7%. The average deviation over all amino acid codons of the *Btt* synthetic gene codon usage from that of dicot plants is 7.8%. In general terms the overall average deviation of the codon usage of a synthetic gene from that of a host cell is calculated using the equation $$A = \sum_{n=1}^{Z} \frac{\frac{X_n - Y_n}{X_n} \times 100}{Z}$$

where $X_n$=frequency of usage for codon n in the host cell; $Y_n$=frequency of usage for codon n in the synthetic gene. Where n represents an individual codon that specifies an amino acid, the total number of codons is Z, which in the preferred embodiment is 61. The overall deviation of the frequency of codon usage, A, for all amino acids should preferably be less than about 25%, and more preferably less than about 10%.

Derived from is used to mean taken, obtained, received, traced, replicated or descended from a source (chemical and/or biological). A derivative may be produced by chemical or biological manipulation (including but not limited to substitution, addition, insertion, deletion, extraction, isolation, mutation and replication) of the original source.

Chemically synthesized, as related to a sequence of DNA, means that the component nucleotides were assembled in vitro. Manual chemical synthesis of DNA may be accomplished using well established procedures (Caruthers, M. (1983) in *Methodology of DNA and RNA Sequencing*, Weissman (ed.), Praeger Publishers, New York, Chapter 1), or automated chemical synthesis can be performed using one of a number of commercially available machines.

The term, designed to be highly expressed as used herein refers to a level of expression of a designed gene wherein the amount of its specific mRNA transcripts produced is sufficient to be quantified in Northern blots and, thus, represents a level of specific mRNA expressed corresponding to greater than or equal to approximately 0.001% of the poly(A)+ mRNA. To date, natural *Bt* genes are transcribed at a level wherein the amount of specific mRNA produced is insufficient to be estimated using the Northern blot technique. However, in the present invention, transcription of a synthetic *Bt* gene designed to be highly expressed not only allows quantification of the specific mRNA transcripts produced but also results in enhanced expression of the translation product which is measured in insecticidal bioassays.

Crystal protein or insecticidal crystal protein or crystal toxin refers to the major protein component of the parasporal crystals formed in strains of *Bt*. This protein component exhibits selective pathogenicity to different species of insects. The molecular size of the major protein isolated from parasporal crystals varies depending on the strain of *Bt* from which it is derived. Crystal proteins having molecular weights of approximately 132, 65, and 28 kDa have been reported. It has been shown that the approximately 132 kDa protein is a protoxin that is cleaved to form an approximately 65 kDa toxin.

The crystal protein gene refers to the DNA sequence encoding the insecticidal crystal protein in either full length protoxin or toxin form, depending on the strain of *Bt* from which the gene is derived.

The authors of this invention observed that expression in plants of *Bt* crystal protein mRNA occurs at levels that are not routinely detectable in Northern blots and that low levels of *Bt* crystal protein expression correspond to this low level of mRNA expression. It is preferred for exploitation of these genes as potential biocontrol methods that the level of expression of *Bt* genes in plant cells be improved and that the stability of *Bt* mRNA in plants be optimized. This will allow greater levels of *Bt* mRNA to accumulate and will result in an increase in the amount of insecticidal protein in plant tissues. This is essential for the control of insects that are relatively resistant to *Bt* protein.

Thus, this invention is based on the recognition that expression levels of desired, recombinant insecticidal protein in transgenic plants can be improved via increased expression of stabilized mRNA transcripts; and that, conversely, detection of these stabilized RNA transcripts may be utilized to measure expression of translational product (protein). This invention provides a means of resolving the problem of low expression of insecticidal protein RNA in plants and, therefore, of low protein expression through the use of an improved, synthetic gene specifying an insecticidal crystal protein from *Bt*.

Attempts to improve the levels of expression of *Bt* genes in plants have centered on comparative studies evaluating parameters such as gene type, gene length, choice of promoters, addition of plant viral untranslated RNA leader, addition of intron sequence and modification of nucleotides surrounding the initiation ATG codon. To date, changes in these parameters have not led to significant enhancement of Bt protein expression in plants. Applicants find that, surprisingly, to express Bt proteins at the desired level in plants, modifications in the coding region of the gene were effective. Structural-function relationships can be studied using site-specific mutagenesis by replacement of restriction fragments with synthetic DNA duplexes containing the desired nucleotide changes (Lo et al. (1984) Proc. Natl. Acad. Sci. 81:2285–2289). However, recent advances in recombinant DNA technology now make it feasible to chemically synthesize an entire gene designed specifically for a desired function. Thus, the Btt coding region was chemically synthesized, modified in such a way as to improve its expression in plants. Also, gene synthesis provides the opportunity to design the gene so as to facilitate its subsequent mutagenesis by incorporating a number of appropriately positioned restriction endonuclease sites into the gene.

The present invention provides a synthetic Bt gene for a crystal protein toxic to an insect. As exemplified herein, this protein is toxic to coleopteran insects. To the end of improving expression of this insecticidal protein in plants, this invention provides a DNA segment homologous to a Btt structural gene and, as exemplified herein, having approximately 85% homology to the Btt structural gene in p544Pst-Met5. In this embodiment the structural gene encoding a Btt insecticidal protein is obtained through chemical synthesis of the coding region. A chemically synthesized gene is used in this embodiment because it best allows for easy and efficacious accommodation of modifications in nucleotide sequences required to achieve improved levels of cross-expression.

Today, in general, chemical synthesis is a preferred method to obtain a desired modified gene. However, to date, no plant protein gene has been chemically synthesized nor has any synthetic gene for a bacterial protein been expressed in plants. In this invention, the approach adopted for synthesizing the gene consists of designing an improved nucleotide sequence for the coding region and assembling the gene from chemically synthesized oligonucleotide segments. In designing the gene, the coding region of the naturally-occurring gene, preferably from the Btt subclone, p544Pst-Met5, encoding a 65 kDa polypeptide having coleoperan toxicity, is scanned for possible modifications which would result in improved expression of the synthetic gene in plants. For example, to optimize the efficiency of translation, codons preferred in highly expressed proteins of the host cell are utilized.

Bias in codon choice within genes in a single species appears related to the level of expression of the protein encoded by that gene. Codon bias is most extreme in highly expressed proteins of E. coli and yeast. In these organisms, a strong positive correlation has been reported between the abundance of an isoaccepting tRNA species and the favored synonymous codon. In one group of highly expressed proteins in yeast, over 96% of the amino acids are encoded by only 25 of the 61 available codons (Bennetzen and Hall (1982) J. Biol. Chem. 257:3026–3031). These 25 codons are preferred in all sequenced yeast genes, but the degree of preference varies with the level of expression of the genes. Recently, Hoekema and colleagues (1987) Mol. Cell. Biol. 7:2914–2924 reported that replacement of these 25 preferred codons by minor codons in the 5' end of the highly expressed yeast gene PGK1 results in a decreased level of both protein and mRNA. They concluded that biased codon choice in highly expressed genes enhances translation and is required for maintaining mRNA stability in yeast. Without doubt, the degree of codon bias is an important factor to consider when engineering high expression of heterologous genes in yeast and other systems.

Experimental evidence obtained from point mutations and deletion analysis has indicated that in eukaryotic genes specific sequences are associated with post-transcriptional processing, RNA destabilization, translational termination, intron splicing and the like. These are preferably employed in the synthetic genes of this invention. In designing a bacterial gene for expression in plants, sequences which interfere with the efficacy of gene expression are eliminated.

In designing a synthetic gene, modifications in nucleotide sequence of the coding region are made to modify the A+T content in DNA base composition of the synthetic gene to reflect that normally found in genes for highly expressed proteins native to the host cell. Preferably the A+T content of the synthetic gene is substantially equal to that of said genes for highly expressed proteins. In genes encoding highly expressed plant proteins, the A+T content is approximately 55%. It is preferred that the synthetic gene have an A+T content near this value, and not sufficiently high as to cause destabilization of RNA and, therefore, lower the protein expression levels. More preferably, the A+T content is no more than about 60% and most preferably is about 55%. Also, for ultimate expression in plants, the synthetic gene nucleotide sequence is preferably modified to form a plant initiation sequence at the 5' end of the coding region. In addition, particular attention is preferably given to assure that unique restriction sites are placed in strategic positions to allow efficient assembly of oligonucleotide segments during construction of the synthetic gene and to facilitate subsequent nucleotide modification. As a result of these modifications in coding region of the native Bt gene, the preferred synthetic gene is expressed in plants at an enhanced level when compared to that observed with natural Bt structural genes.

In specific embodiments, the synthetic Bt gene of this invention encodes a Btt protein toxic to coleopteran insects. Preferably, the toxic polypeptide is about 598 amino acids in length, is at least 75% homologous to a Btt polypeptide, and, as exemplified herein, is essentially identical to the protein encoded by p544Pst-Met5, except for replacement of threonine by alanine at residue 2. This amino acid substitution results as a consequence of the necessity to introduce a guanine base at position +4 in the coding sequence.

In designing the synthetic gene of this invention, the coding region from the Btt subclone, p544Pst-Met5, encoding a 65 kDa polypeptide having coleopteran toxicity, is scanned for possible modifications which would result in improved expression of the synthetic gene in plants. For example, in preferred embodiments, the synthetic insecticidal protein is strongly expressed in dicot plants, e.g., tobacco, tomato, cotton, etc., and hence, a synthetic gene under these conditions is designed to incorporate to advantage codons used preferentially by highly expressed dicot proteins. In embodiments where enhanced expression of insecticidal protein is desired in a monocot, codons preferred by highly expressed monocot proteins (given in Table 1) are employed in designing the synthetic gene.

In general, genes within a taxonomic group exhibit similarities in codon choice, regardless of the function of these genes. Thus an estimate of the overall use of the genetic code by a taxonomic group can be obtained by summing codon frequencies of all its sequenced genes. This species-specific codon choice is reported in this invention from analysis of 208 plant genes. Both monocot and dicot plants are analyzed individually to determine whether these broader taxonomic groups are characterized by different patterns of synonymous codon preference. The 208 plant genes included in the codon analysis code for proteins having a wide range of functions and they represent 6 monocot and 36 dicot species. These proteins are present in different plant tissues at varying levels of expression.

In this invention it is shown that the relative use of synonymous codons differs between the monocots and the dicots. In general, the most important factor in discriminating between monocot and dicot patterns of codon usage is the percentage G+C content of the degenerate third base. In monocots, 16 of 18 amino acids favor G+C in this position, while dicots only favor G+C in 7 of 18 amino acids.

The G ending codons for Thr, Pro, Ala and Ser are avoided in both inonocots and dicots because they contain C in codon position II. The CG dinucleotide is strongly avoided in plants (Boudraa (1987) Genet. Sel. Evol. 19:143–154) and other eukaryotes (Grantham et al. (1985) Bull. Inst. Pasteur 83:95–148), possibly due to regulation involving methylation. In dicots, XCG is always the least favored codon, while in monocots this is not the case. The doublet TA is also avoided in codon positions II and III in most eukaryotes, and this is true of both nonocots and dicots.

Grantham and colleagues (1986) Oxford Surveys in Evol. Biol. 3:48–81 have developed two codon choice indices to quantify CG and TA doublet avoidance in codon positions II and III. XCG/XCC is the ratio of codons having C as base II of G-ending to C-ending triplets, while XTA/XTT is the ratio of A-ending to T-ending triplets with T as the second base. These indices have been calculated for the plant data in this paper (Table 2) and support the conclusion that monocot and dicot species differ in their use of these dinucleotides.

TABLE 2

Avoidance of CG and TA doublets in codons position II–III.
XCG/XCC and XTA/XAA values are multiplied by 100.

| Group | Plants | Di-cots | Mono-cots | Maize | Soy-bean | RuBPC SSU | CAB |
|---|---|---|---|---|---|---|---|
| XCG/XCC | 40 | 30 | 61 | 67 | 37 | 18 | 22 |
| XTA/XTT | 37 | 35 | 47 | 43 | 41 | 9 | 13 |

RuBPC SSU = ribulose 1,5 bisphosphate small subunit
CAB = chlorophyll a/b binding protein Additionally, for two species, soybean and maize, species-specific codon usage profiles were calculated (not shown). The maize codon usage pattern resembles that of monocots in general, since these sequences represent over half of the monocot sequences available. The codon profile of the maize subsample is even more strikingly biased in its preference for G+C in codon position III. On the other hand, the soybean codon usage pattern is almost identical to the general dicot pattern, even though it represents a much smaller portion of the entire dicot sample.

In order to determine whether the coding strategy of highly expressed genes such as the ribulose 1,5 bisphosphate small subunit (RuBPC SSU) and chlorophyll a/b binding protein (CAB) is more biased than that of plant genes in general, codon usage profiles for subsets of these genes (19 and 17 sequences, respectively) were calculated (not shown). The RuBPC SSU and CAB pooled samples are characterized by stronger avoidance of the codons XCG and XTA than in the larger monocot and dicot samples (Table 2). Although most of the genes in these subsamples are dicot in origin (17/19 and 15/17), their codon profile resembles that of the monocots in that G+C is utilized in the degenerate base III.

The use of pooled data for highly expressed genes may obscure identification of species-specific patterns in codon choice. Therefore, the codon choices of individual genes for RuBPC SSU and CAB were tabulated. The preferred codons of the maize and wheat genes for RuBPC SSU and CAB are more restricted in general than are those of the dicot species. This is in agreement with Matsuoka et al. (1987) J. Biochem. 102:673–676) who noted the extreme codon bias of the maize RuBPC SSU gene as well as two other highly expressed genes in maize leaves, CAB and phosphoenolpyruvate carboxylase. These genes almost completely avoid the use of A+T in codon position III, although this codon bias was not as pronounced in non-leaf proteins such as alcohol dehydrogenase, zein 22 kDa sub-unit, sucrose synthetase and ATP/ADP translocator. Since the wheat SSU and CAB genes have a similar pattern of codon preference, this may reflect a common monocot pattern for these highly expressed genes in leaves. The CAB gene for Lemna and the RUBPC SSU genes for Chlamdomonas share a similar extreme preference for G+C in codon position III. In dicot CAB genes, however, A+T degenerate bases are preferred by some synonymous codons (e.g., GCT for Ala, CTT for Leu, GGA and GGT for Gly). In general, the G+C preference is less pronounced for both RuBPC SSU and CAB genes in dicots than in monocots.

In designing a synthetic gene for expression in plants, attempts are also made to eliminate sequences which interfere with the efficacy of gene expression. Sequences such as the plant polyadenylation signals, e.g., AATAAA, polymerase II termination sequence, e.g., $CAN_{(7-9)}AGTNNAA$, UCUUCGG hairpins and plant consensus splice sites are highlighted and, if present in the native Btt coding sequence, are modified so as to eliminate potentially deleterious sequences.

Modifications in nucleotide sequence of the *Btt* coding region are also preferably made to reduce the A+T content in DNA base composition. The *Btt* coding region has an A+T content of 64%, which is about 10% higher than that found in a typical plant coding region. Since A+T-rich regions typify plant intergenic regions and plant regulatory regions, it is deemed prudent to reduce the A+T content. The synthetic *Btt* gene is designed to have an A+T content of 55%, in keeping with values usually found in plants.

Also, a single modification (to introduce guanine in lieu of adenine) at the fourth nucleotide position in the *Btt* coding sequence is made in the preferred embodiment to form a sequence consonant with that believed to function as a plant initiation sequence (Taylor et al. (1987) Mol. Gen. Genet. 210:572–577) in optimization of expression. In addition, in exemplifying this invention thirty-nine nucleotides (thirteen codons) are added to the coding region of the synthetic gene in an attempt to stabilize primary transcripts. However, it appears that equally stable transcripts are obtained in the absence of this extension polypeptide containing thirty-nine nucleotides.

Not all of the above-mentioned modifications of the natural *Bt* gene must be made in constructing a synthetic *Bt* gene in order to obtain enhanced expression. For example, a synthetic gene may be synthesized for other purposes in addition to that of achieving enhanced levels of expression. Under these conditions, the original sequence of the natural *Bt* gene may be preserved within a region of DNA corresponding to one or more, but not all, segments used to construct the synthetic gene. Depending on the desired purpose of the gene, modification may encompass substitution of one or more, but not all, of the oligonucleotide segments used to construct the synthetic gene by a corresponding region of natural *Bt* sequence.

As is known to those skilled in the art of synthesizing genes (Mandecki et al. (1985) Proc. Natl. Acad. Sci. 82:3543–3547; Feretti et al. (1986) Proc. Natl. Acad. Sci. 83:599–603), the DNA sequence to be synthesized is divided into segment lengths which can be synthesized conveniently and without undue complication. As exemplified herein, in preparing to synthesize the Btt gene, the coding region is divided into thirteen segments (A–M). Each segment has unique restriction sequences at the cohesive ends. Segment A, for example, is 228 base pairs in length and is constructed from six oligonucleotide sections, each containing approximately 75 bases. Single-stranded oligonucleotides are annealed and ligated to form DNA. segments. The length of the protruding cohesive ends in complementary oligonucleotide segments is four to five residues. In the strategy evolved for gene synthesis, the sites designed for the joining of oligonucleotide pieces and DNA segments are different from the restriction sites created in the gene.

In the specific embodiment, each DNA segment is cloned into a pIC-20 vector for amplification of the DNA. The nucleotide sequence of each fragment is determined at this stage by the dideoxy method using the recombinant phage DNA as templates and selected synthetic oligonucleotides as primers.

As exemplified herein and illustrated schematically in FIGS. 3 and 4, each segment individually (e.g., segment M) is excised at the flanking restriction sites from its cloning vector and spliced into the vector containing segment A. Most often, segments are added as a paired segment instead of as a single segment to increase efficiency. Thus, the entire gene is constructed in the original plasmid harboring segment A. The nucleotide sequence of the entire gene is determined and found to correspond exactly to that shown in FIGS. 1A–C.

In preferred embodiments the synthetic *Btt* gene is expressed in plants at an enhanced level when compared to that observed with natural *Btt* structural genes. To that end, the synthetic structural gene is combined with a promoter functional in plants, the structural gene and the promoter region being in such position and orientation with respect to each other that the structural gene can be expressed in a cell in which the promoter region is active, thereby forming a functional gene. The promoter regions include, but are not limited to, bacterial and plant promoter regions. To express the promoter region/structural gene combination, the DNA segment carrying the combination is contained by a cell. Combinations which include plant promoter regions are contained by plant cells, which, in turn, may be contained by plants or seeds. Combinations which include bacterial promoter regions are contained by bacteria, e.g., *Bt* or *E. coli*. Those in the art will recognize that expression in types of micro-organisms other than bacteria may in some circumstances be desirable and, given the present disclosure, feasible without undue experimentation.

The recombinant DNA molecule carrying a synthetic structural gene under promoter control can be introduced into plant tissue by any means known to those skilled in the art. The technique used for a given plant species or specific type of plant tissue depends on the known successful techniques. As novel means are developed for the stable insertion of foreign genes into plant cells and for manipulating the modified cells, skilled artisans will be able to select from known means to achieve a desired result. Means for introducing recombinant DNA into plant tissue include, but are not limited to, direct DNA uptake (Paszkowski, J. et al. (1984) EMBO J. 3:2717), electroporation (Fromm, M. et al. (1985) Proc. Natl. Acad. Sci. USA 82:5824), microinjection (Crossway, A. et al. (1986) Mol. Gen. Genet. 202:179), or T-DNA mediated transfer from *Agrobacterium tumefaciens* to the plant tissue. There appears to be no fundamental limitation of T-DNA transformation to the natural host range of Agrobacterium. Successful T-DNA-mediated transformation of monocots (Hooykaas-Van Slogteren, G. et al. (1984) Nature 311:763), gymnosperm (Dandekar, A. et al. (1987) Biotechnology 5:587) and algae (Ausich, R., EPO application 108,580) has been reported. Representative T-DNA vector systems are described in the following references: An, G. et al. (1985) EMBO J. 4:277; Herrera-Estrella, L. et al. (1983) Nature 303:209; Herrera-Estrella, L. et al. (1983) EMBO J. 2:987; Herrera-Estrella, L. et al. (1985) in *Plant Genetic Engineering*, New York: Cambridge University Press, p. 63. Once introduced into the plant tissue, the expression of the structural gene may be assayed by any means known to the art, and expression may be measured as mRNA transcribed or as protein synthesized. Techniques are known for the in vitro culture of plant tissue, and in a number of cases, for regeneration into whole plants. Procedures for transferring the introduced expression complex to commercially useful cultivars are known to those skilled in the art.

In one of its preferred embodiments the invention disclosed herein comprises expression in plant cells of a synthetic insecticidal structural gene under control of a plant expressible promoter, that is to say, by inserting the insecticide structural gene into T-DNA under control of a plant expressible promoter and introducing the T-DNA containing the insert into a plant cell using known means. Once plant cells expressing a synthetic insecticidal structural gene under control of a plant expressible promoter are obtained, plant tissues and whole plants can be regenerated therefrom using methods and techniques well-known in the art. The regenerated plants are then reproduced by conventional means and the introduced genes can be transferred to other strains and cultivars by conventional plant breeding techniques.

The introduction and expression of the synthetic structural gene for an insecticidal protein can be used to protect a crop from infestation with common insect pests. Other uses of the invention, exploiting the properties of other insecticide structural genes introduced into other plant species will be readily apparent to those skilled in the art. The invention in principle applies to. introduction of any synthetic insecticide structural gene into any plant species into which foreign DNA (in the preferred embodiment T-DNA) can be introduced and in which said DNA can remain stably replicated. In general, these taxa presently include, but are not limited to, gymnosperms and dicotyledonous plants, such as sunflower (family Compositeae), tobacco (family Solanaceae), alfalfa, soybeans and other legumes (family Leguminoseae), cotton (family Malvaceae), and most vegetables, as well as monocotyledonous plants. A plant containing in its tissues increased levels of insecticidal protein will control less susceptible types of insect, thus providing advantage over present insecticidal uses of *Bt*. By incorporation of the insecticidal protein into the tissues of a plant, the present invention additionally provides advantage over present uses of insecticides by eliminating instances of nonuniform application and the costs of buying and applying insecticidal preparations to a field. Also, the present invention eliminates the need for careful timing of application of such preparations since small larvae are most sensitive to insecticidal protein and the protein is always present, minimizing crop damage that would otherwise result from preapplication larval foraging.

This invention combines the specific teachings of the present disclosure with a variety of techniques and expedients known in the art. The choice of expedients depends on variables such as the choice of insecticidal protein from a Bt strain, the extent of modification in preferred codon usage, manipulation of sequences considered to be destabilizing to RNA or sequences prematurely terminating transcription, insertions of restriction sites within the design of the synthetic gene to allow future nucleotide modifications, addition of introns or enhancer sequences to the 5' and/or 3' ends of the synthetic structural gene, the promoter region, the host in which a promoter region/structural gene combination is expressed, and the like. As novel insecticidal proteins and toxic polypeptides are discovered, and as sequences responsible for enhanced cross-expression (expression of a foreign structural gene in a given host) are elucidated, those of ordinary skill will be able to select among those elements to produce "improved" synthetic genes for desired-proteins having agronomic value. The fundamental aspect of the present invention is the ability to synthesize a novel gene coding for an insecticidal protein, designed so that the protein will be expressed at an enhanced level in plants, yet so that it will retain its inherent property of insect toxicity and retain or increase its specific insecticidal activity.

EXAMPLES

The following Examples are presented as illustrations. of embodiments of the present invention. They do not limit the scope of this invention, which is determined by the claims.

The following strains were deposited with the Patent Culture Collection, Northern Regional Research Center, 1815 N. University Street, Peoria, Ill. 61604.

| Strain | Deposited on | Accession # |
| --- | --- | --- |
| E. coli MC1061 (p544-HindIII) | 6 October 1987 | NRRL B-18257 |
| E. coli MC1061 (p544Pst-Met5) | 6 October 1987 | NRRL B-18258 |

The deposited strains are provided for the convenience of those in the art, and are not necessary to practice the present invention, which may be practiced with the present disclosure in combination with publicly available protocols, information, and materials. E. coli MC1061, a good host for plasmid transformations, was disclosed by Casadaban, M. J. and Cohen, S. N. (1980) J. Mol. Biol. 138:179–207.

Example 1

Design of the Synthetic Insecticidal Crystal Protein Gene (i) Preparation of Toxic Subclones of the Btt Gene Construction, isolation, and characterization of pNSB544 is disclosed by Sekar, V. et al. (1987) Proc. Natl. Acad. Sci. USA 84:7036–7040, and Sekar, V. and Adang, M. J., U.S. patent application Ser. No. 108,285, filed Oct. 13, 1987, which is hereby incorporated by reference. A 3.0 kbp HindIII fragment carrying the crystal protein gene of pNSBP544 is inserted into the HindIII site of pIC-2OH (Marsh, J. L. et al. (1984) Gene 32:481–485), thereby yielding a plasmid designated p544-HindIII, which is on deposit. Expression in E. coli yields a 73 kDa crystal protein in addition to the 65 kDa species characteristic of the crystal protein obtained from Btt isolates.

A 5.9 kbp BamHI fragment carrying the crystal protein gene is removed from pNSBP544 and inserted into BamHI-linearized pIC-2OH DNA. The resulting plasmid, p405/44-7, is digested with BglII and religated, thereby removing Bacillus sequences flanking the 3'-end of the crystal protein gene. The resulting plasmid, p405/54-12, is digested with PstI and religated, thereby removing Bacillus sequences flanking the 5'-end of the crystal protein and about 150 bp from the 5'-end of the crystal protein structural gene. The resulting plasmid, p405/81-4, is digested with SphI and PstI and is mixed with and ligated to a synthetic linker having the following structure:

```
         SD           MetThrAla     (SEQ ID NO:5)
    5'CAGGATCCAACAATGACTGCA3'
  3'GTACGTCCTAGGTTGTTACTG5'
    SphI                     PstI
```

(SD indicates the location of a Shine-Dalgarno prokaryotic ribosome binding site.) The resulting plasmid, p544Pst-Met5, contains a structural gene encoding a protein identical to one encoded by pNSBP544 except for a deletion of the amino-terminal 47 amino acid residues. The nucleotide sequence of the Btt coding region in p544Pst-Met5 is presented in FIG. 1. In bioassays (Sekar and Adang, U.S. patent application Ser. No. 108,285, supra), the proteins encoded by the full-length Btt gene in pNSBP544 and the N-terminal deletion derivative, p544Pst-Met5, were shown to be equally toxic. All of the plasmids mentioned above have their crystal protein genes in the same orientation as the lacZ gene of the vector.

(ii) Modification of Preferred Codon Usage

Table 1 presents the frequency of codon usage for (A) dicot proteins, (B) Bt proteins, (C) the synthetic Btt gene, and (D) monocot proteins. Although some codons for a particular amino acid are utilized to approximately the same extent by both dicot and Bt proteins (e.g., the codons for serine), for the most part, the distribution of codon frequency varies significantly between dicot and Bt proteins, as illustrated in columns A and B in Table 1.

TABLE 1

Frequency of Codon Usage

| | | Distribution Fraction | | | |
| --- | --- | --- | --- | --- | --- |
| Amino Acid | Codon | (A)Dicot Genes | (B)Bt Genes | (C)Synthetic Btt Gene | (D)Monocot Genes |
| Gly | GGG | 0.12 | 0.08 | 0.13 | 0.21 |
| Gly | GGA | 0.38 | 0.53 | 0.37 | 0.17 |
| Gly | GGT | 0.33 | 0.24 | 0.34 | 0.18 |
| Gly | GGC | 0.16 | 0.16 | 0.16 | 0.43 |
| Glu | GAG | 0.51 | 0.13 | 0.52 | 0.75 |
| Glu | GAA | 0.49 | 0.87 | 0.48 | 0.25 |
| Asp | GAT | 0.58 | 0.68 | 0.56 | 0.27 |
| Asp | GAC | 0.42 | 0.32 | 0.44 | 0.73 |
| Val | GTG | 0.29 | 0.15 | 0.30 | 0.36 |
| Val | GTA | 0.12 | 0.32 | 0.10 | 0.08 |
| Val | GTT | 0.39 | 0.29 | 0.35 | 0.19 |
| Val | GTC | 0.20 | 0.24 | 0.25 | 0.37 |
| Ala | GCG | 0.06 | 0.12 | 0.06 | 0.22 |
| Ala | GCA | 0.25 | 0.50 | 0.24 | 0.16 |
| Ala | GCT | 0.42 | 0.32 | 0.41 | 0.24 |
| Ala | GCC | 0.27 | 0.06 | 0.29 | 0.38 |
| Lys | AAG | 0.61 | 0.13 | 0.58 | 0.86 |
| Lys | AAA | 0.39 | 0.87 | 0.42 | 0.14 |
| Asn | AAT | 0.45 | 0.79 | 0.44 | 0.25 |
| Asn | AAC | 0.55 | 0.21 | 0.56 | 0.75 |
| Met | ATG | 1.00 | 1.00 | 1.00 | 1.00 |
| Ile | ATA | 0.18 | 0.30 | 0.20 | 0.11 |
| Ile | ATT | 0.45 | 0.57 | 0.43 | 0.24 |
| Ile | ATC | 0.37 | 0.13 | 0.37 | 0.64 |
| Thr | ACG | 0.08 | 0.14 | 0.07 | 0.20 |
| Thr | ACA | 0.27 | 0.68 | 0.27 | 0.14 |
| Thr | ACT | 0.35 | 0.14 | 0.34 | 0.19 |

TABLE 1-continued

Frequency of Codon Usage

| | | | | | |
|---|---|---|---|---|---|
| Thr | ACC | 0.30 | 0.05 | 0.32 | 0.46 |
| Trp | TGG | 1.00 | 1.00 | 1.00 | 1.00 |
| End | TGA | 0.33 | 0.00 | 0.00 | 0.34 |
| Cys | TGT | 0.44 | 0.33 | 0.33 | 0.30 |
| Cys | TGC | 0.56 | 0.67 | 0.67 | 0.70 |
| End | TAG | 0.19 | 0.00 | 0.00 | 0.36 |
| End | TAA | 0.48 | 1.00 | 1.00 | 0.30 |
| Tyr | TAT | 0.43 | 0.81 | 0.43 | 0.21 |
| Tyr | TAC | 0.57 | 0.19 | 0.57 | 0.79 |
| Phe | TTT | 0.45 | 0.75 | 0.44 | 0.25 |
| Phe | TTC | 0.55 | 0.25 | 0.56 | 0.75 |
| Ser | AGT | 0.14 | 0.25 | 0.13 | 0.08 |
| Ser | AGC | 0.18 | 0.13 | 0.19 | 0.26 |
| Ser | TCG | 0.06 | 0.08 | 0.06 | 0.14 |
| Ser | TCA | 0.19 | 0.19 | 0.17 | 0.11 |
| Ser | TCT | 0.25 | 0.25 | 0.27 | 0.15 |
| Ser | TCC | 0.18 | 0.10 | 0.17 | 0.25 |
| Arg | AGG | 0.25 | 0.09 | 0.23 | 0.26 |
| Arg | AGA | 0.30 | 0.50 | 0.32 | 0.09 |
| Arg | CGG | 0.04 | 0.14 | 0.05 | 0.13 |
| Arg | CGA | 0.08 | 0.14 | 0.09 | 0.04 |
| Arg | CGT | 0.21 | 0.09 | 0.23 | 0.12 |
| Arg | CGC | 0.11 | 0.05 | 0.09 | 0.36 |
| Gln | CAG | 0.41 | 0.18 | 0.39 | 0.46 |
| Gln | CAA | 0.59 | 0.82 | 0.61 | 0.54 |
| His | CAT | 0.54 | 0.90 | 0.50 | 0.33 |
| His | CAC | 0.46 | 0.10 | 0.50 | 0.67 |
| Leu | TTG | 0.26 | 0.08 | 0.27 | 0.14 |
| Leu | TTA | 0.10 | 0.46 | 0.12 | 0.03 |
| Leu | CTG | 0.09 | 0.04 | 0.10 | 0.28 |
| Leu | CTA | 0.08 | 0.21 | 0.10 | 0.10 |
| Leu | CTT | 0.28 | 0.15 | 0.18 | 0.15 |
| Leu | CTC | 0.19 | 0.06 | 0.22 | 0.31 |
| Pro | CCG | 0.09 | 0.20 | 0.08 | 0.23 |
| Pro | CCA | 0.42 | 0.56 | 0.44 | 0.34 |
| Pro | CCT | 0.32 | 0.24 | 0.32 | 0.17 |
| Pro | CCC | 0.17 | 0.00 | 0.16 | 0.26 |

154 coding sequences of dicot nuclear genes were used to compile the codon usage table. The pooled dicot coding sequences, obtained from Genbank (release 55) or, when no Genbank file name is specified, directly from the published source, were:

| GENUS/SPECIES | GENBANK | PROTEIN | REF |
|---|---|---|---|
| Antirrhinum majus | AMACHS | Chalcone synthetase | |
| Arabidopsis thaliana | ATHADH | Alcohol dehydrogenase | |
| | ATHH3GA | Histone 3 gene 1 | |
| | ATHH3GB | Histone 3 gene 2 | |
| | ATHH4GA | Histone 4 gene 1 | |
| | ATHLHCP1 | CAB | |
| | ATHTUBA | α tubulin | |
| | | 5-enolpyruvyl4hifate 3-phosphate synthetase | 1 |
| Bertholletia excelsa | | High methionine storage protein | 2 |
| Brassica campestris | | Acyl carrier protein | 3 |
| Brassica napus | BNANAP | Napin | |
| Brassica oleacea | BOLSLSGR | S-locus specific glycoprotein | |
| Canavalia ensiformis | CENCONA | Concanavalin A | |
| Carica papaya | CPAPAP | Papain | |
| Chlamdomonas reinhardtii | CREC552 | Preapocytochrome | |
| | CRERBCS1 | RuBPC small subunit gene 1 | |
| | CRERBCS2 | RuBPC small subunit gene 2 | |
| Cucurbita pepo | CUCPHT | Phytochrome | |
| Cucumis sativus | CUSGMS | Glyoxosomal malate synthetase | |
| | CUSLHCPA | CAB | |
| | CUSSSU | RuBPC small subunit | |
| Daucus carota | DAREXT | Extensin | |
| | DAREXTR | 33 kD extensin related protein | |
| Dolichos biflorus | DBILECS | seed lectin | |
| Flaveria trinervia | FTRBCR | RuBPC small subunit | |
| Glycine max | SOY7SAA | 7S storage protein | |
| | SOYACT1G | Actin 1 | |
| | SOYCIIPI | CII protease inhibitor | |
| | SOYGLYA1A | Glycinin A1a Bx subunits | |
| | SOYGLYAAB | Glycinin A5A4B3 subunits | |
| | SOYGLYAB | Glycinin A3/b4 subunits | |
| | SOYGLYR | Glycinin A2B1a subunits | |
| | SOYHSP175 | Low M W heat shock proteins | |
| | SOYLGBI | Leghemoglobin | |
| | SOYLEA | Lectin | |
| | SOYOX | Lipoxygenase 1 | |
| | SOYNOD20G | 20 kDa nodulin | |
| | SOYNOD23G | 23 kDa nodulin | |
| | SOYNOD24H | 24 kDa nodulin | |
| | SOYNOD26B | 26 kDa nodulin | |
| | SOYNOD26R | 26 kDa nodulin | |
| | SOYNOD27R | 27 kDa nodulin | |
| | SOYNOD35M | 35 kDa nodulin | |
| | SOYNOD75 | 75 kDa nodulin | |
| | SOYNODR1 | Nodulin C51 | |
| | SOYNODR2 | Nodulin E27 | |
| | SOYPRP1 | Proline rich protein | |
| | SOYRUBP | RuBPC small subunit | |
| | SOYURA | Urease | |
| | SOYHSP26A | Heat shock protein 26A | |
| | | Nuclear-encoded chloroplast heat shock protein | 4 |
| | | 22 kDa nodulin | 5 |
| | | β1 tubulin | 6 |
| | | β2 tubulin | 6 |
| Gossypium hirsutum | | Seed α globulin (vicilin) | 7 |
| | | Seed β globulin (vicilin) | 7 |
| Helianthus annus | HNNRUBCS | RuBPC small subunit | |
| | | 2S albumin seed storage protein | 8 |
| Ipomoea batatas | | Wound-induced catalase | 9 |
| Lemna gibba | LGIAB19 | CAB | |
| | LGIR5BPC | RuBPC small subunit | |
| Lupinus luteus | LUPLBR | leghemoglobin I | |
| Lycopersicon esculentum | TOMBIOBR | Biotin binding protein | |
| | TOMETHYBR | Ethylene biosynthesis protein | |
| | TOMPG2AR | Polygalacturonase-2a | |
| | TOMPSI | Tomato photosystem I protein | |
| | TOMRBCSA | RuBPC small subunit | |
| | TOMRBCSB | RuBPC small subunit | |
| | TOMRBCSC | RuBPC small subunit | |
| | TOMRBCSD | RuBPC small subunit | |
| | TOMRRD | Ripening related protein | |
| | TOMWIPIG | Wound induced proteinase inhibitor I | |
| | TOMWIPII | Wound induced proteinase inhibitor II | |
| | | CAB 1A | 10 |
| | | CAB 1B | 10 |
| | | CAB 3C | 10 |
| | | CAB 4 | 11 |
| | | CAB 5 | 11 |
| Medicago sativa | ALFLB3R | Leghemoglobin III | |
| Mesembryanthemum crystallinum | | RuBPC small subunit | 12 |

TABLE 1-continued

Frequency of Codon Usage

| | | | |
|---|---|---|---|
| Nicotiana plumbaginifolia | TOBATP21 | Mitochondrial ATP synthase β subunit | |
| | | Nitrate reductase | 13 |
| | | Glutamine synthetase | 14 |
| Nicotiana tabacum | TOBECH | Endochitinase | |
| | TOBGAPA | A subunit of chloroplast G3PD | |
| | TOBGAPB | B subunit of chloroplast G3PD | |
| | TOBGAPC | C subunit of chloroplast G3PD | |
| | TOBPR1AR | Pathogenesis related protein 1a | |
| | TOBPR1CR | Pathogenesis-related protein 1c | |
| | TOBPRPR | Pathogenesis related protein 1b | |
| | TOBPXDLF | Peroxidase | |
| | TOBRBPCO | RuBPC small subunit | |
| | TOBTHAUR | TMV-induced protein homologous to thaumatin | |
| Perseus americana | AVOCEL | Cellulase | |
| Petroselinum hortense | PHOCHL | Chalcone synthase | |
| Petunia sp. | PETCAB13 | CAB 13 | |
| | PETCAB22L | CAB 22L | |
| | PETCAB22R | CAB 22R | |
| | PETCAB25 | CAB 25 | |
| | PETCAB37 | CAB 37 | |
| | PETCAB91R | CAB 91R | |
| | PETCHSR | Chalcone synthase | |
| | PETGCR1 | Glycine-rich protein | |
| | PETRBCS08 | RuBPC small subunit | |
| | PETRBCS11 | RuBPC small subunit | |
| | | 70 kDa heat shock protein | 15 |
| Phascolus vulgaris | PHVCHM | Chitinase | |
| | PHVDLECA | Phytohemogglutinin E | |
| | PHVDLECB | Phytohemagglutinin L | |
| | PHVGSR1 | Glutamine synthetase 1 | |
| | PHVGSR2 | Glutamine synthetase 2 | |
| | PHVLBA | Leghemogobin | |
| | PHVLECT | Lectin | |
| | PHVPAL | Phenylalanine ammonia lyase | |
| | PHVPHASAR | α phaseolin | |
| | PHVPHASBR | β phaseolin | |
| | | Arcelin seed protein | 16 |
| | | Chalcone synthase | 17 |
| Pisum sativum | PEAALB2 | Seed albumin | |
| | PEACAB80 | CAB | |
| | PEAGSR1 | Glutamine synthetase (nodule) | |
| | PEALECA | Lectin | |
| | PEALEGA | Legumin | |
| | PEARUBPS | RuBPC small subunit | |
| | PEAVIC2 | Vicilin | |
| | PEAVIC4 | Vicilin | |
| | PEAVIC7 | Vicilin | |
| | | Alcohol dehydrogenase 1 | 18 |
| | | Glutamine synthetase (leaf) | 19 |
| | | Glutamine synthetase (root) | 19 |
| | | Histone 1 | 20 |
| | | Nuclear encoded chloroplast heat shock protein | 4 |
| Raphanus sativus | | RuBPC small subunit | 21 |
| Ricinus communis | RCCAGG | Agglutinin | |
| | RCCRICIN | Ricin | |
| | RCCICL4 | Isocitrate lyase | |
| Silene pratensis | SIPFDX | Ferrodoxin precursor | |
| Solanum tuberosum | POTPAT | Patatin | |
| | POTINHWI | Wound-induced proteinase inhibitor | |
| | POTLS1G | Light-inducible tissue specific ST-LS1 gene | |
| | POTI2G | Wound-induced proteinase inhibitor II | |
| | POTRBCS | RuBPC small subunit | |
| | | Sucrose synthetase | 22 |
| Spinacia oleracea | SPIACPI | Acyl carrier protein 1 | |
| | SPIOEC16 | 16 kDa photosynthetic oxygen-evolving protein | |
| | SPIOEC23 | 23 kDa photosynthetic oxygen-evolving protein | |
| | SPIPCG | Plastocyanin | |
| | SPIPS33 | 33 kDa photosynthetic water oxidation complex precursor | |
| | | Glycolate oxidase | 23 |
| Vicia faba | VFALBA | Leghemoglobin | |
| | VFALEB4 | Legumin B | |
| | | Vicillin | 24 |

Pooled 53 monocot coding sequences obtained from Genbank (release 55) or, when no Genbank file name is specified, directly from the published source, were:

| GENUS/SPECIES | GENBANK | PROTEIN | REF |
|---|---|---|---|
| Avena sallva | ASTAP3R | Phytochrome 3 | |
| Hordeum vulgare | BLYALR | Aleurain | |
| | BLYAMY1 | α amylase 1 | |
| | BLYAMY2 | α amylase 2 | |
| | BLYCHORD1 | Hordein C | |
| | BLYGLUCB | β glucanase | |
| | BLYHORB | B1 hordein | |
| | BLYPAPI | Amylase/protease inhibitor | |
| | BLYTH1AR | Toxin α hordothionin | |
| | BLYUBIQR | Ubiquitin | |
| | | Histone 3 | 25 |
| | | Leaf specific thionin 1 | 26 |
| | | Leaf specific thionin 2 | 26 |
| | | Plastocyanin | 27 |
| Oryta sativa | RICGLUTG | Glutelin | |
| | | Glutelin | 28 |
| Triticum aestivum | WHTAMYA | α amylase | |
| | WHTCAB | CAB | |
| | WHTEMR | Em protein | |
| | WHTGIR | gibberellin responsive protein | |
| | WHTGLGB | γ gliadin | |
| | WHTGLIABA | α/β gliadin Class AII | |
| | WHTGLUT1 | High MW glutenin | |
| | WHTH3 | Histone 3 | |
| | WHTH4091 | Histone 4 | |
| | WHTRBCB | RuBPC small subunit | |
| Secale cereale | RYESECGSR | γ secalin | |
| Zea mays | MZEA1G | 40.1 kD A1 protein (NADPH-dependent reductase) | |
| | MZEACT1G | Actin | |
| | MZEADH11F | Alcohol dehydrogenase 1 | |
| | MZEADH2NR | Alcohol dehydrogenase 2 | |
| | MZEALD | Aldolase | |
| | MZEANT | ATP/ADP translocator | |
| | MZEEG2R | Glutelin 2 | |
| | MZEGGST3B | Glutathione S transferase | |
| | MZEH3C2 | Histone 3 | |
| | MZEH4C14 | Histone 4 | |
| | MZEHSP701 | 70 kD Heat shock protein, exon 1 | |

TABLE 1-continued

Frequency of Codon Usage

| | |
|---|---|
| MZEHSP702 | 70 kD Heat shock protein, exon 2 |
| MZELHCP | CAB |
| MZEMPL3 | Lipid body surface protein L3 |
| MZEPEPCR | Phosphoenolyruvate carboxylase |
| MZERBCS | RuBPC small subunit |
| MZESUSYSG | Sucrose synthetase |
| MZETPI2 | Triosephosphate isomerase 1 |
| MZEZEA20M | 19 kD zein |
| MZEZEA30M | 19 kD zein |
| MZEZE15A3 | 15 kD zein |
| MZEZE16 | 16 kD zein |
| MZEZE19A | 19 kD zein |
| MZEZE22A | 22 kD zein |
| MZEZE22B | 22 kD zein |
| | Catalase 2     29 |
| | Regulatory C1 locus     30 |

Bt codons were obtained from analysis of coding sequences of the following genes:
Bt var. kurstaki HD-73, 6.6 kb HindIII fragment (Kronstad et al. (1983) J. Bacteriol. 154:419–428);
Bt var. kurstaki HD-1, 5.3 kb fragment (Adang et al. (1987) in Biotechnology in Invertebrate Pathology and Cell Culture, K. Maramorosh (ed.), Academic Press, Inc. New York, pp. 85–99);
Bt var. kurstaki HD-1, 4.5 kb fragment (Schnepf and Whiteley (1985) J. Biol. Chem. 260:6273–6280); and
Bt var. tenebrionis, 3.0 kb HindIII fragment (Sekar et al. (1987) Proc. Natl. Acad. Sci. 84:7036–7040).
REFERENCES
1. Klee, H. J. et al. (1987) Mol. Gen. Genet. 210:437–442.
2. Altenbach, S. B. et al. (1987) Plant Mol. Biol. 8:239–250.
3. Rose, R. E. et al. (1987) Nucl. Acids Res. 15:7197.
4. Vierling, E. et al. (1988) EMBO J. 7:575–581.
5. Sandal, N. N. et al. (1987) Nucl. Acids Res. 15:1507–1519.
6. Tingey, S. V. et al. (1987) EMBO J. 6:1–9.
7. Chlan, C. A. et al. (1987) Plant Mol. Biol. 9:533–546.
8. Allen, R. D. et al. (1987) Mol. Gen. Genet. 210:211–218.
9. Sakajo, S. et al. (1987) Eur. J. Biochem. 165:437–442.
10. Pirersky, E. et al. (1987) Plant Mol. Biol. 9:109–120.
11. Ray, J. et al. (1987) Nucl. Acids Res. 15:10587.
12. DeRocjer, E. J. et al. (1987) Nucl. Acids Res. 15:6301.
13. Calza, R. et al. (1987) Mol. Gen. Genet. 209:552–562.
14. Tingey, S. V. and Coruzzi, G. M. (1987) Plant Phys. 84:366–373.
15. Winter, J. et al. (1988) Mol. Gen. Genet. 211:315–319.
16. Osborn, T. C. et al. (1988) Science 240:207–210.
17. Ryder, T. B. et al. (1987) Mol. Gen. Genet. 210:219–233.
18. Llewellyn, D. J. et al. (1987) J. Mol. Biol. 195:115–123.
19. Tingey, S. V. et al. (1987) EMBO J. 6:1–9.
20. Gantt, J. S. and Key, J. L. (1987) Eur. J. Biochem. 166:119–125.
21. Guidet, F. and Fourcroy, P. (1988) Nucl. Acids Res. 16:2336.
22. Salanoubat, M. and Belliard, G. (1987) Gene 60:47–56.
23. Volokita, M. and Somerville, C. R. (1987) J. Biol. Chem. 262:15825–15828.
24. Bassner, R. et al. (1987) Nucl. Acids Res. 15:9609.
25. Chojecki, J. (1986) Carlsberg Res. Commun. 51:211–217.
26. Bohlmann, H. and Apel, K. (1987) Mol. Gen. Genet. 207:446–454.
27. Nielsen, P. S. and Gausing, K. (1987) FEBS Lett. 225:159–162.
28. Higuchi, W. and Fukazawa, C. (1987) Gene 55:245–253.
29. Bethards, L. A. et al. (1987) Proc. Natl. Sci. USA 84:6830–6834.
30. Paz-Ares, J. et al. (1987) EMBO J. 6:3553–3558.

For example, dicots utilize the AAG codon for lysine with a frequency of 61% and the AAA codon with a frequency of 39%. In contrast, in *Bt* proteins the lysine codons AAG and AAA are used with a frequency of 13% and 87%, respectively. It is known in the art that seldom used codons are generally detrimental to that system and must be avoided or used judiciously. Thus, in designing a synthetic gene encoding the *Btt* crystal protein, individual amino acid codons found in the original *Btt* gene are altered to reflect the codons preferred by dicot genes for a particular amino acid. However, attention is given to maintaining the overall distribution of codons for each amino acid within the coding region of the gene. For example, in the case of alanine, it can be seen from Table 1 that the codon GCA is used in *Bt* proteins with a frequency of 50%, whereas the codon GCT is the preferred codon in dicot proteins. In designing the synthetic *Btt* gene, not all codons for alanine in the original *Bt* gene are replaced by GCT; instead, only some alanine codons are changed to GCT while others are replaced with different alanine codons in an attempt to preserve the overall distribution of codons for alanine used in dicot proteins. Column C in Table 1 documents that this goal is achieved; the frequency of codon usage in dicot proteins (column A) corresponds very closely to that used in the synthetic *Btt* gene (column C).

In similar manner, a synthetic gene coding for insecticidal crystal protein can be optimized for enhanced expression in monocot plants. In Table 1, column D, is presented the frequency of codon usage of highly expressed monocot proteins.

Because of the degenerate nature of the genetic code, only part of the variation contained in a gene is expressed in this protein. It is clear that variation between degenerate base frequencies is not a neutral phenomenon since systematic codon preferences have been reported for bacterial, yeast and mammalian genes. Analysis of a large group of plant gene sequences indicates that synonymous codons are used differently by monocots and dicots. These patterns are also distinct from those reported for *E. coli*, yeast and man.

In general, the plant codon usage pattern more closely resembles that of man and other higher eukaryotes than unicellular organisms, due to the overall preference for G+C content in codon position III. Monocots in this sample share the most commonly used codon for 13 of 18 amino acids as that reported for a sample of human genes (Grantham et al. (1986 supra), although dicots favor the most commonly used human codon in only 7 of 18 amino acids.

Discussions of plant codon usage have focused on the differences between codon choice in plant nuclear genes and in chloroplasts. Chloroplasts differ from higher plants in that they encode only 30 tRNA species. Since chloroplasts have restricted their tRNA genes, the use of preferred codons by chloroplast-encoded proteins appears more extreme. However, a positive correlation has been reported between the level of isoaccepting tRNA for a given amino acid and the frequency with which this codon is used in the chloroplast genome (Pfitzinger et al. (1987) Nucl. Acids Res. 15:1377–1386).

Our analysis of the plant genes sample confirms earlier reports that the nuclear and chloroplast genomes in plants have distinct coding strategies. The codon usage of monocots in this sample is distinct from chloroplast usage, sharing the most commonly used codon for only 1 of 18 amino acids. Dicots in this sample share the most commonly used codon of chloroplasts in only 4 of 18 amino acids. In general, the chloroplast codon profile more closely resembles that of unicellular organisms, with a strong bias towards the use of A+T in the degenerate third base.

In unicellular organisms, highly expressed genes use a smaller subset of codons than do weakly expressed genes although the codons preferred are distinct in some cases. Sharp and Li (1986) Nucl. Acids Res. 14:7734–7749 report that codon usage in 165 *E. coli* genes reveals a positive correlation between high expression and increased codon bias. Bennetzen and Hall (1982) supra have described a similar trend in codon selection in yeast. Codon usage in these highly expressed genes correlates with the abundance of isoaccepting tRNAs in both yeast and *E coli*. It has been proposed that the good fit of abundant yeast and *E. coli* mRNA codon usage to isoacceptor tRNA abundance promotes high translation levels and high steady state levels of these proteins. This strongly suggests that the potential for high levels of expression of plant genes in yeast or *E. coli* is limited by their codon usage. Hoekema et al. (1987) supra report that replacement of the 25 most favored yeast codons with rare codons in the 5' end of the highly expressed gene PGK1 leads to a decrease in both mRNA and protein. These results indicate that codon bias should be emphasized when engineering high expression of foreign genes in yeast and other systems.

(iii) Sequences within the *Btt* Coding Region having Potentially Destabilizing Influences Analysis of the *Btt* gene reveals that the A+T content represents 64% of the DNA base composition of the coding region. This level of A+T is about 10% higher than that found in a typical plant coding region. Most often, high A+T regions are found in intergenic regions. Also, many plant regulatory sequences are observed to be AT-rich. These observations lead to the consideration that an elevated A+T content within the *Btt* coding region may be contributing to a low expression level in plants. Consequently, in designing a synthetic *Btt* gene, the A+T content is decreased to more closely approximate the A+T levels found in plant proteins. As illustrated in Table 3, the A+T content is lowered to a level in keeping with that found in coding regions of plant nuclear genes. The synthetic *Btt* gene of this invention has an A+T content of 55%.

TABLE 3

Adenine + Thymine Content in Btt Coding Region

| Coding Region | Base | | | | | |
|---|---|---|---|---|---|---|
| | G | A | T | C | % G + C | % A + T |
| Natural Btt gene | 341 | 633 | 514 | 306 | 36 | 64 |
| Synthetic Btt gene | 392 | 530 | 483 | 428 | 45 | 55 |

In addition, the natural *Btt* gene is scanned for sequences that are potentially destabilizing to *Btt* RNA. These sequences, when identified in the original *Btt* gene, are eliminated through modification of nucleotide sequences. Included in this group of potentially destabilizing sequences are:

(a) plant polyadenylation signals (as described by Joshi (1987) Nucl. Acids Res. 15:9627–9640). In eukaryotes, the primary transcripts of nuclear genes are extensively processed (steps including 5'-capping, intron splicing, polyadenylation) to form mature and translatable mRNAs. In higher plants, polyadenylation involves endocucleolytic cleavage at the polyA site followed by the addition of several A residues to the cleaved end. The selection of the polyA site is presumed to be cis-regulated. During expression of *Bt* protein and RNA in different plants, the present inventors have observed that the polyadenylated mRNA isolated from these expression systems is not full-length but instead is truncated or degraded. Hence, in the present invention it was decided to minimize possible destabilization of RNA through elimination of potential polyadenylation signals within the coding region of the synthetic *Btt* gene. Plant polyadenylation signals including AATAAA, AATGAA, AATAAT, AATATT, GATAAA, GATAAA, and AATAAG motifs do not appear in the synthetic *Btt* gene when scanned for 0 mismatches of the sequences.

(b) polymerase II termination sequence, $CAN_{7-9}$ AGT-NNAA. This sequence was shown (Vankan and Filipowicz (1988) EMBO J. 7:791–799) to be next to the 3' end of the coding region of the U2 snRNA genes of *Arabidopsis thaliana* and is believed to be important for transcription termination upon 3' end processing. The synthetic *Btt* gene is devoid of this termination sequence.

(c) CUUCGG hairpins, responsible for extraordinarily stable RNA secondary structures associated with various biochemical processes (Tuerk et al. (1988) Proc. Natl. Acad. Sci. 85:1364–1368). The exceptional stability of CUUCGG hairpins suggests that they have an unusual structure and may function in organizing the proper folding of complex RNA structures. CUUCGG hairpin sequences are not found with either 0 or 1 mismatches in the *Btt* coding region.

(d) plant consensus splice sites, 5'=AAG:GTAAGT(SEQ ID NO:6) and 3'=TTTT(Pu)TTT(Pu)T(Pu)T(Pu)T(Pu) TGCAG:C(SEQ ID NO:7), as described by Brown et al. (1986) EMBO J. 5:2749–2758. Consensus sequences for the 5' and 3' splice junctions have been derived from 20 and 30 plant intron sequences, respectively. Although it is not likely that such potential splice sequences are present in *Bt* genes, a search was initiated for sequences resembling plant consensus splice sites in the synthetic *Btt* gene. For the 5' splice site, the closest match was with three mismatches. This gave 12 sequences of which two had G:GT. Only position 948 was changed because 1323 has the KpnI site needed for reconstruction. The 3'-splice site is not found in the synthetic *Btt* gene.

Thus, by highlighting potential RNA-destabilizing sequences, the synthetic *Btt* gene is designed to eliminate known eukaryotic regulatory sequences that affect RNA synthesis and processing.

Example 2

Chemical Synthesis of a Modified *Btt* Structural Gene (i) Synthesis Strategy

The general plant for synthesizing linear double-stranded DNA sequences coding for the crystal protein from *Btt* is schematically simplified in FIG. 2. The optimized DNA coding sequence (FIGS. 1A–C) is divided into thirteen segments (segments A–M) to be synthesized individually, isolated and purified. As shown in FIG. 2, the general strategy begins by enzymatically joining segments A and M to form segments AM to which is added segment BL to form segment ABLM. Segment CK is then added enzymatically to make segment ABCKLM which is enlarged through addition of segments DJ, EI and RFH sequentially to give finally the total segment ABCDEFGHIJKLM, representing the entire coding region of the *Btt* gene.

Figure 3:
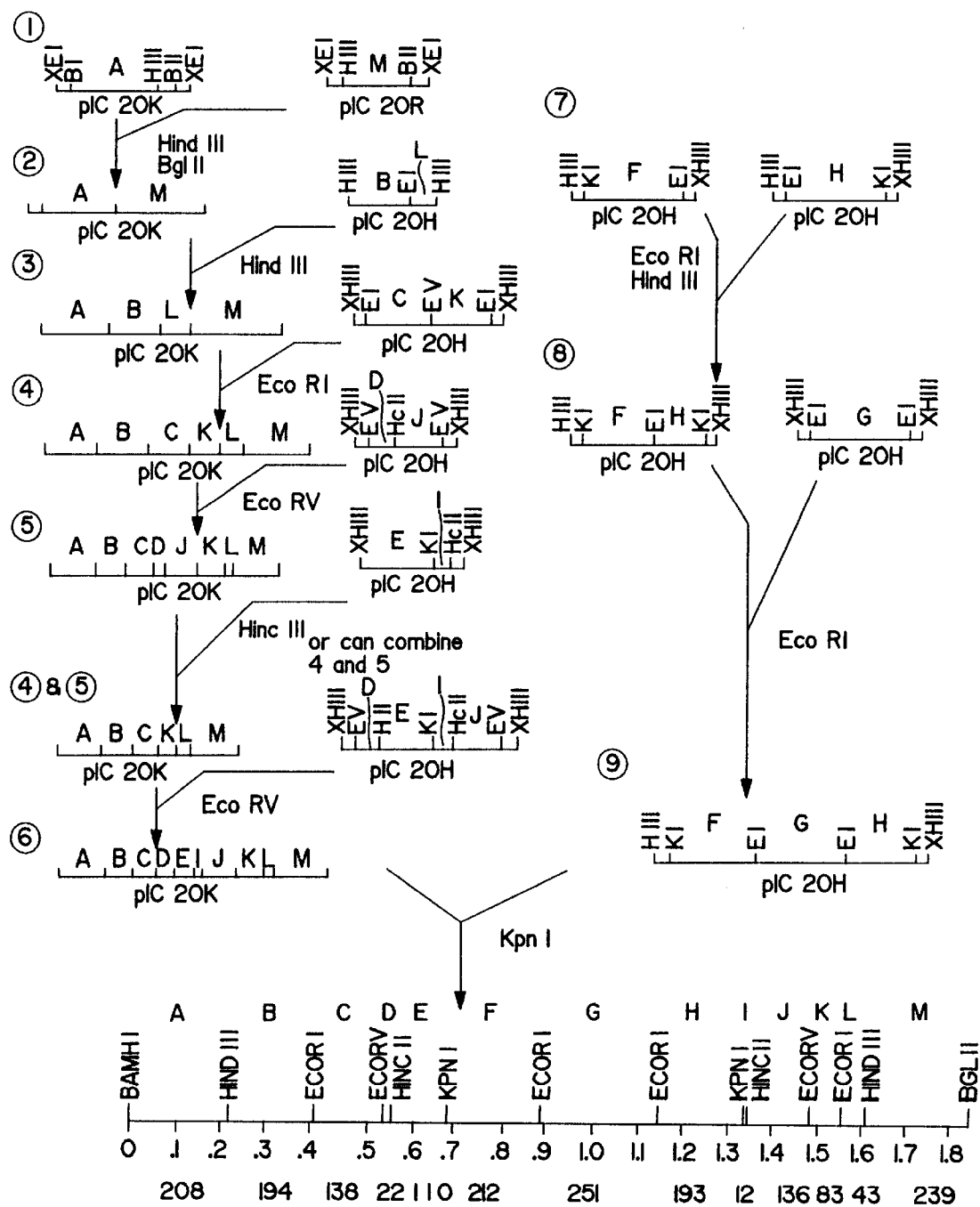
FIG. 3 is a schematic diagram showing the assembly of oligonucleotide segments in the construction of a synthetic Btt gene. Each segment (A through M) is built from oligonucleotides of different sizes, annealed and liated to form the desired DNA segment.

FIG. 3 outlines in more detail the strategy used in combining individual DNA segments in order to effect the synthesis of a gene having unique restriction sites integrated into a defined nucleotide sequence. Each of the thirteen segments (A to M) has unique restriction sites at both ends, allowing the segment to be strategically spliced into a growing DNA polymer. Also, unique sites are placed at each end of the gene to enable easy transfer from one vector to another.

The thirteen segments (A to N) used to construct the synthetic gene vary in size. oligonucleotide pairs of approximately 75 nucleotides each are used to construct larger segments having approximately 225 nucleotide pairs. FIG. 3 documents the number of base pairs contained within each segment and specifies the unique restriction sites bordering each segment. Also, the overall strategy to incorporate specific segments at appropriate splice sites is detailed in FIG. 3.

(ii) Preparation of Oligodeoxynucleotides

Preparation of oligodeoxynucleotides for use in the synthesis of a DNA sequence comprising a gene for Btt is carried out according to the general procedures described by Matteucci et al. (1981) J. Am. Chem. Soc. 103:3185–3192 and Beaucage et al. (1981) Tetrahedron Lett. 22:1859–1862. All oligonucleotides are prepared by the solid-phase phosphoramidite triester coupling approach, using an Applied Biosystems Model 380A DNA synthesizer. Deprotection and cleavage of the oligomers from the solid support are carried out according to standard procedures. Crude oligonucleotide mixtures are purified using an oligonucleotide purification cartridge (OTC, Applied Biosystems) as described by McBride et al. (1988) Biotechniques 6:362–367.

5'-phosphorylation of oligonucleotides is performed with T4 polynucleotide kinase. The reaction contains 2 μg oligonucleotide and 18.2 units polynucleotide kinase (Pharmacia) in linker kinase buffer (Maniatis (1982) *Cloning Manual*, Fritsch and Sambrook (eds.), Cold Spring Harbor Laboratory, Cold Spring Harbor, N.Y.). The reaction is incubated at 37° C. for 1 hour.

Oligonucleotides are annealed by first heating to 95° C. for 5 min. and then allowing complementary pairs to cool slowly to room temperature. Annealed pairs are reheated to 65° C., solutions are combined, cooled slowly to room temperature and kept on ice until used. The ligated mixture may be purified by electrophoresis through a 4% NuSieve agarose (FMC) gel. The band corresponding to the ligated duplex is excised, the DNA is extracted from the agarose and ethanol precipitated.

Ligations are carried out as exemplified by that used in M segment ligations. M segment DNA is brought to 65° C. for 25 min, the desired vector is added and the reaction mixture is incubated at 65° C. for 15 min. The reaction is slow cooled over 1½ hours to room temperature. ATP to 0.5 mM and 3.5 units of T4 DNA ligase salts are added and the reaction mixture is incubated for 2 hr at room temperature and then maintained overnight at 15° C. The next morning, vectors which had not been ligated to M block DNA were removed upon linearization by EcoRI digestion. Vectors ligated to the M segment DNA are used to transform *E. coli* MC1061. Colonies containing inserted blocks are identified by colony hybridization with $^{32}P$-labelled oligonucleotide probes. The sequence of the DNA segment is confirmed by isolating plasmid DNA and sequencing using the dideoxy method of Sanger et al. (1977) Proc. Natl. Acad. Sci. 74:5463–5467.

(iii) Synthesis of Segment AM

Three oligonucleotide pairs (A1 and its complementary strand A1c, A2 and A2c and A3 and A3c) are assembled and ligated as described above to make up segment A. The nucleotide sequence of segment A is as follows:

TABLE 4

Nucleotide Sequence of Segment A

```
       BamHI
       XhoII              PstI
         |                  |
    AATTGGGATCCAACAATGGCTGCAGACAACAACACGGAGGCCCTCGATAGCTCTACCACC
  1 ---------+---------+---------+---------+---------+---------+  60
        CCCTAGGTTGTTACCGACGTCTGTTGTTGTGCCTCCGGGAGCTATCGAGATGGTGG
EcoR1 end
                   M  A  A  D  N  N  T  E  A  L  D  S  S  T  T A1 (71 bases)
                                                                     -------------
                                                                     A1c* (76 bases)

AAAGATGTCATTCAGAAGGGCATCTCCGTTGTGGGTGATCTCCTTGGCGTTGTTGGTTTC
 61 ---------+---------+---------+---------+---------+---------+ 120
    TTTCTACAGTAAGTCTTCCCGTAGAGGCAACACCCACTAGAGGAACCGCAACAACCAAAG

K  D  V  I  Q  K  G  I  S  V  V  G  D  L  L  G  V  V  G  F

A2 (75 bases)
                 BspXII                                              -------------
            BanI    |                                                A2c (76 bases)
              |     |
    CCCTTTGGTGGTGCCCTTGTTTCGTTCTACACTAACTTTCTGAATACTATTTGGCCCAGC
121 ---------+---------+---------+---------+---------+---------+ 180
    GGGAAACCACCACGGGAACAAAGCAAGATGTGATTGAAAGACTTATGATAAACCGGGTCG

P  F  G  G  A  L  V  S  F  Y  T  N  F  L  N  T  I  W  P  S

XhoII                    A3 (82 bases)
                                            BglII  EcoRI             -------------
                                    HindIII  |  XbaI |               A3c (76 bases)
                                       |     |    |  |  end
    GAAGACCCTTGGAAGGCTTTTATGGAGCAAGTGGAAGCTTAGATCTAG
181 ---------+---------+---------+---------+---------+-- 232
    CTTCTGGGAACCTTCCGAAAATACCTCGTTCACCTTCGAATCTAGATCTTAA

E  D  P  W  K  A  F  M  E  Q  V  E
```

*c = complementary strand.

In Table 4, bold lines demarcate the individual oligonucleotides. Fragment A1 contains 71 bases, A1c has 76 bases, A2 has 75 bases, A2c has 76 bases, A3 has 82 bases and A3c has 76 bases. In all, segment A is composed of 228 base pairs and is contained between EcoRI restriction enzyme site and one destroyed EcoRI site (5')J. (Additional restriction sites within Segment A are indicated.) The EcoRI single-stranded cohesive ends allow segment A to be annealed and then ligated to the EcoRI-cut cloning vector, pIC20K.

Segment M comprises three oligonucleotide pairs: M1, 80 bases, M1c, 86 bases, M2, 87 bases, M2c, 87 bases, M3, 85 bases and M3c 79 bases. The individual oligonucleotides are annealed and ligated according to standard procedures as described above. The overall nucleotide sequence of segment M is:

As proposed in FIG. 3, segment M is joined to segment A in the plasmid in which it is contained. Segment M is excised at the flanking restrictions sites from its cloning vector and spliced into pIC20K, harboring segment A, through successive digestions with HindIII followed by BglII. The pIC20K vector now comprises segment A joined to segment M with a HindIII site at the splice site (see FIG. 3). Plasmid pIC20K is derived from pIC20R by removing the ScaI-NdeI DNA fragment and inserting a HincII fragment containing an NPTI coding region. The resulting plasmid of 4.44 kb confers resistance to kanamycin on *E. coli.*

Example 3
Expression of Synthetic Crystal Protein Gene in Bacterial Systems

The synthetic *Btt* gene is designed so that it is expressed in the pIC20R-kan vector in which it is constructed. This expression is produced utilizing the initiation methionine of the lacZ protein of pIC20K. The wild-type *Btt* crystal protein sequence expressed in this manner has full insecticidal activity. In addition, the synthetic gene is designed to contain a BamHI site 5' proximal to the initiating methionine codon and a BglII site 3' to the terminal TAG translation stop codon. This facilitates the cloning of the insecticidal crystal

TABLE 5

Nucleotide Sequence of Segment M

```
     HindIII          BspXII
Eco     |           BanII|
RI-end  |               ||
    AATTAAGCTTGGACGGGGCTCCATTCAACCAATACTACTTCGATAAGACCATCAACAAAG
  1 ---------+---------+---------+---------+---------+---------+  60
        TTCGAACCTGCCCCGAGGTAAGTTGGTTATGATGAAGCTATTCTGGTAGTTGTTTC S  L  D  G  A  P  F  N  Q  Y  Y  F  D  K  T  I  N  K  G
                                                                        M1 (80 bases)
                                                                        --------------
                                                                        M1c* (86 bases)
                                                      AsuII
                                                        |
    GAGACACACTCACGTATAATTCCTTCAACTTAGCCAGCTTCAGCACTCCATTCGAATTGT
 61 ---------+---------+---------+---------+---------+---------+ 120
    CTCTGTGTGAGTGCATATTAAGGAAGTTGAATCGGTCGAAGTCGTGAGGTAAGCTTAACA D  T  L  T  Y  N  S  F  N  L  A  S  F  S  T  P  F  E  L  S
                                                                        M2 (87 bases)
                                                                        --------------
                                                                        M2c (87 bases)
                                                         AccI
                        AhaII                      TthI   |
                          |                          |    |
    CAGGGAACAACTTGCAGATAGGCGTCACAGGATTGAGTGCTGGTGACAAGGTCTACATCG
121 ---------+---------+---------+---------+---------+---------+ 180
    GTCCCTTGTTGAACGTCTATCCGCAGTGTCCTAACTCACGACCACTGTTCCAGATGTAGC

G  N  N  L  Q  I  G  V  T  G  L  S  A  G  D  K  V  Y  I  D

MstII
                                                 |
    ACAAGATTGAGTTCATTCCAGTGAACCTTAGGTCCCCAGGAACCGAGCTTGAGTTCATCG
181 ---------+---------+---------+---------+---------+---------+ 240
    TGTTCTAACTCAAGTAAGGTCACTTGGAATCCAGGGGTCCTTGGCTCGAACTCAAGTAGC

K  I  E  F  I  P  V  N  L  R  S  P  G  T  E  L  E  F  I  D
                                                                        M3 (85 bases)
                                                                        --------------
                                                                        M3c (79 bases)
       BglII
       XhoII
     XbaI |
       |  |
    ACATCTAGATCT
241 ---------+------ 256                                              252 BASES (TOTAL)
    TGTAGATCTAGATTAA
```

*c = complementary strand

In Table 5 bold lines demarcate the individual oligonucleotides. Segment M contains 252 base pairs and has destroyed EcoRI, restriction sites at both ends. (Additional restriction sites within segment M are indicated). Segment M is inserted into vector pIC20R at an EcoRI restriction site and cloned.

protein coding region into bacterial expression vectors such as pDR540 (Russell and Bennett, 1982). Plasmid pDR540 contains the TAC promoter which allows the production of proteins including Btt crystal protein under controlled conditions in amounts up to 10% of the total bacterial protein. This promoter functions in many gram-negative bacteria including E. coli and Pseudomonas.

Production of Bt insecticidal crystal protein from the synthetic gene in bacteria demonstrates that the protein produced has the expected toxicity to coleopteran insects. These recombinant bacterial strains in themselves have potential value as microbial insecticides, product of the synthetic gene.

Example 4

Expression of a Synthetic Crystal Protein Gene in Plants

The synthetic Btt crystal protein gene is designed to facilitate cloning into the expression cassettes. These utilize sites compatible with the BamHI and BglII restriction sites flanking the synthetic gene. Cassettes are available that utilize plant promoters including CaMV 35S, CaMV 19S and the ORF 24 promoter from T-DNA. These cassettes provide the recognition signals essential for expression of proteins in plants. These cassettes are utilized in the micro Ti plasmids such as pH575. Plasmids such as pH575 containing the synthetic Btt gene directed by plant expression signals are utilized in disarmed Agrobacterium tumefaciens to introduce the synthetic gene into plant genomic DNA. This system has been described previously by Adang et al. (1987) to express Bt var. kurstaki crystal protein gene in tobacco plants. These tobacco plants were toxic to feeding tobacco hornworms.

Example 5

Assay for Insecticidal Activity

Bioassays are conducted essentially as described by Sekar, V. et al. supra. Toxicity is assessed by an estimate of the $LD_{50}$. Plasmids are grown in E. coli JM105 (Yanisch-Perron, C. et al. (1985) Gene 33:103–119). On a molar basis, no significant differences in toxicity are observed between crystal proteins encoded by p544Pst-Met5, p544-HindIII, and pNSBP544. When expressed in plants under identical conditions, cells containing protein encoded by the synthetic gene are observed to be more toxic than those containing protein encoded by the native Btt gene. Immunoblots ("western" blots) of cell cultures indicated that those that are more toxic have more crystal protein antigen. Improved expression of the synthetic Btt gene relative to that of a natural Btt gene is seen as the ability to quantitate specific mRNA transcripts from expression of synthetic Btt genes on Northern blot assays.

We claim:

1. A synthetic *Bacillus thuringiensis* (*B.t.*) gene which is expressed in descendant plant cells and encodes a pesticidal protein toxin, wherein said synthetic *B.t.* gene is produced by the process of:

selecting a *B.t.* pesticidal protein toxin desired to be expressed in a plant cell;

obtaining a table indicating codon usage bias for a gene or genes more highly expressed in a plant cell than a native *B.t.* gene;

using said table to design a modified coding sequence which encodes said protein toxin, whereby said modified coding sequence has a frequency of codon usage that more closely resembles the frequency of codon usage of the plant cell in which it is to be expressed than did the native *B.t.* coding sequence encoding said protein toxin, said modified coding sequence having at least about 10% of the nucleotides changed as compared to the native *B.t.* coding sequence;

obtaining a synthetic *B.t.* gene comprising a coding region comprising said modified coding sequence wherein said coding region is under the control of a plant-expressible promoter;

introducing said synthetic *B.t.* gene into a plant cell;

culturing said cell to obtain descendant plant cells or plants comprising descendant plant cells, said descendant plant cells comprising said synthetic *B.t.* gene; and establishing that said synthetic *B.t.* gene is expressed in said descendant plant cells.

2. The synthetic *Bacillus thuringiensis* gene of claim 1, comprising an A+T base content of less than about 60%.

3. The synthetic *Bacillus thuringiensis* gene of claim 1, wherein the process of producing said synthetic gene contains the additional step of determining the frequency of codon usage of said modified coding sequence.

4. A method of designing a synthetic *Bacillus thuringiensis* (*B.t.*) gene which is expressed in descendant plant cells, comprising the steps of:

selecting a *B.t.* pesticidal protein toxin desired to be expressed in a plant cell;

obtaining a table indicating codon usage bias for a gene or genes more highly expressed in a plant cell than a native *B.t.* gene;

using said table to design a modified coding sequence which encodes said protein toxin, whereby said modified coding sequence has a frequency of codon usage that more closely resembles the frequency of codon usage of the plant cell in which it is to be expressed than did the native *B.t.* coding sequence encoding said protein toxin, said modified coding sequence having at least about 10% of the nucleotides changed as compared to the native *B.t.* coding sequence;

obtaining a synthetic *B.t.* gene comprising a coding region comprising said modified coding sequence wherein said coding region is under the control of a plant-expressible promoter;

introducing said synthetic *B.t.* gene into a plant cell;

culturing said cell to obtain descendant plant cells, said descendant plant cells comprising said synthetic *B.t.* gene; and establishing that said synthetic *B.t.* gene is expressed in said descendant plant cells.

5. The method of claim 4, wherein said synthetic gene comprises an A+T base content of less than about 60%.

6. The method of claim 4, wherein said method further comprises the step of determining the frequency of codon usage of said modified coding sequence.

* * * * *

UNITED STATES PATENT AND TRADEMARK OFFICE
CERTIFICATE OF CORRECTION

PATENT NO.     : 6,015,891
DATED          : January 18, 2000
INVENTOR(S)    : Michael J. Adang, Elizabeth E. Murray Page 1 of 1

It is certified that error appears in the above-identified patent and that said Letters Patent is hereby corrected as shown below:

Column 4,
Line 42: "FIGS. 1A and 1B" should read -- Figures 1A, 1B and 1C --;
Line 58: "liated" should read -- ligated --.

Column 5,
Line 67: "nay" should read -- may --.

Column 7,
Line 30: "call" should read -- cell --.

Column 11,
Line 15: "inonocots" should read -- monocots --;
Line 23: "nonocots" should read -- monocots --.

Column 15,
Line 27: "illustrations. of" should read -- illustrations of --.

Signed and Sealed this

Eleventh Day of September, 2001

Attest:

*Nicholas P. Godici*

NICHOLAS P. GODICI
*Attesting Officer*        *Acting Director of the United States Patent and Trademark Office*

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1794 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATGACTGCAG ATAATAATAC GGAAGCACTA GATAGCTCTA CAACAAAAGA TGTCATTCAA      60

AAAGGCATTT CCGTAGTAGG TGATCTCCTA GGCGTAGTAG GTTTCCCGTT TGGTGGAGCG     120

CTTGTTTCGT TTTATACAAA CTTTTTAAAT ACTATTTGGC CAAGTGAAGA CCCGTGGAAG     180

GCTTTTATGG AACAAGTAGA AGCATTGATG GATCAGAAAA TAGCTGATTA TGCAAAAAAT     240

AAAGCTCTTG CAGAGTTACA GGGCCTTCAA AATAATGTCG AAGATTATGT GAGTGCATTG     300

AGTTCATGGC AAAAAAATCC TGTGAGTTCA CGAAATCCAC ATAGCCAGGG GCGGATAAGA     360

GAGCTGTTTT CTCAAGCAGA AAGTCATTTT CGTAATTCAA TGCCTTCGTT TGCAATTTCT     420

GGATACGAGG TTCTATTTCT AACAACATAT GCACAAGCTG CCAACACACA TTTATTTTTA     480

CTAAAAGACG CTCAAATTTA TGGAGAAGAA TGGGGATACG AAAAAGAAGA TATTGCTGAA     540

TTTTATAAAA GACAACTAAA ACTTACGCAA GAATATACTG ACCATTGTGT CAAATGGTAT     600

AATGTTGGAT TAGATAAATT AAGAGGTTCA TCTTATGAAT CTTGGGTAAA CTTTAACCGT     660

TATCGCAGAG AGATGACATT AACAGTATTA GATTTAATTG CACTATTTCC ATTGTATGAT     720
```

-continued

```
GTTCGGCTAT ACCCAAAAGA AGTTAAAACC GAATTAACAA GAGACGTTTT AACAGATCCA      780

ATTGTCGGAG TCAACAACCT TAGGGGCTAT GGAACAACCT TCTCTAATAT AGAAAATTAT      840

ATTCGAAAAC CACATCTATT TGACTATCTG CATAGAATTC AATTTCACAC GCGGTTCCAA      900

CCAGGATATT ATGGAAATGA CTCTTTCAAT TATTGGTCCG GTAATTATGT TTCAACTAGA      960

CCAAGCATAG GATCAAATGA TATAATCACA TCTCCATTCT ATGGAAATAA ATCCAGTGAA     1020

CCTGTACAAA ATTTAGAATT TAATGGAGAA AAAGTCTATA GAGCCGTAGC AAATACAAAT     1080

CTTGCGGTCT GGCCGTCCGC TGTATATTCA GGTGTTACAA AAGTGGAATT TAGCCAATAT     1140

AATGATCAAA CAGATGAAGC AAGTACACAA ACGTACGACT CAAAAAGAAA TGTTGGCGCG     1200

GTCAGCTGGG ATTCTATCGA TCAATTGCCT CCAGAAACAA CAGATGAACC TCTAGAAAAG     1260

GGATATAGCC ATCAACTCAA TTATGTAATG TGCTTTTTAA TGCAGGGTAG TAGAGGAACA     1320

ATCCCAGTGT TAACTTGGAC ACATAAAAGT GTAGACTTTT TTAACATGAT TGATTCGAAA     1380

AAAATTACAC AACTTCCGTT AGTAAAGGCA TATAAGTTAC AATCTGGTGC TTCCGTTGTC     1440

GCAGGTCCTA GGTTTACAGG AGGAGATATC ATTCAATGCA CAGAAAATGG AAGTGCGGCA     1500

ACTATTTACG TTCACCGGA TGTGTCGTAC TCTCAAAAAT ATCGAGCTAG AATTCATTAT     1560

GCTTCTACAT CTCAGATAAC ATTTACACTC AGTTTAGACG GGCACCATT TAATCAATAC      1620

TATTTCGATA AACGATAAA TAAGGAGAC ACATTAACGT ATAATTCATT TAATTTAGCA      1680

AGTTTCAGCA CACCATTCGA ATTATCAGGG AATAACTTAC AAATAGGCGT CACAGGATTA     1740

AGTGCTGGAG ATAAAGTTTA TATAGACAAA ATTGAATTTA TTCCAGTGAA TTAA          1794
```

(2) INFORMATION FOR SEQ ID NO:2:

(i) SEQUENCE CHARACTERISTICS:
        (A) LENGTH: 597 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Val Ser Ser Arg Asn
            100                 105                 110

Pro His Ser Gln Gly Arg Ile Arg Glu Leu Phe Ser Gln Ala Glu Ser
        115                 120                 125

His Phe Arg Asn Ser Met Pro Ser Phe Ala Ile Ser Gly Tyr Glu Val
    130                 135                 140

Leu Phe Leu Thr Thr Tyr Ala Gln Ala Ala Asn Thr His Leu Phe Leu
145                 150                 155                 160
```

-continued

```
Leu Lys Asp Ala Gln Ile Tyr Gly Glu Glu Trp Gly Tyr Lys Glu
            165                 170                 175
Asp Ile Ala Glu Phe Tyr Lys Arg Gln Leu Lys Leu Thr Gln Glu Tyr
            180                 185                 190
Thr Asp His Cys Val Lys Trp Tyr Asn Val Gly Leu Asp Lys Leu Arg
            195                 200                 205
Gly Ser Ser Tyr Glu Ser Trp Val Asn Phe Asn Arg Tyr Arg Arg Glu
        210                 215                 220
Met Thr Leu Thr Val Leu Asp Leu Ile Ala Leu Phe Pro Leu Tyr Asp
225                 230                 235                 240
Val Arg Leu Tyr Pro Lys Glu Val Lys Thr Glu Leu Thr Arg Asp Val
                245                 250                 255
Leu Thr Asp Pro Ile Val Gly Val Asn Asn Leu Arg Gly Tyr Gly Thr
            260                 265                 270
Thr Phe Ser Asn Ile Glu Asn Tyr Ile Arg Lys Pro His Leu Phe Asp
        275                 280                 285
Tyr Leu His Arg Ile Gln Phe His Thr Arg Phe Gln Pro Gly Tyr Tyr
        290                 295                 300
Gly Asn Asp Ser Phe Asn Tyr Trp Ser Gly Asn Tyr Val Ser Thr Arg
305                 310                 315                 320
Pro Ser Ile Gly Ser Asn Asp Ile Ile Thr Ser Pro Phe Tyr Gly Asn
                325                 330                 335
Lys Ser Ser Glu Pro Val Gln Asn Leu Glu Phe Asn Gly Glu Lys Val
            340                 345                 350
Tyr Arg Ala Val Ala Asn Thr Asn Leu Ala Val Trp Pro Ser Ala Val
        355                 360                 365
Tyr Ser Gly Val Thr Lys Val Glu Phe Ser Gln Tyr Asn Asp Gln Thr
        370                 375                 380
Asp Glu Ala Ser Thr Gln Thr Tyr Asp Ser Lys Arg Asn Val Gly Ala
385                 390                 395                 400
Val Ser Trp Asp Ser Ile Asp Gln Leu Pro Pro Glu Thr Thr Asp Glu
                405                 410                 415
Pro Leu Glu Lys Gly Tyr Ser His Gln Leu Asn Tyr Val Met Cys Phe
            420                 425                 430
Leu Met Gln Gly Ser Arg Gly Thr Ile Pro Val Leu Thr Trp Thr His
        435                 440                 445
Lys Ser Val Asp Phe Phe Asn Met Ile Asp Ser Lys Lys Ile Thr Gln
        450                 455                 460
Leu Pro Leu Val Lys Ala Tyr Lys Leu Gln Ser Gly Ala Ser Val Val
465                 470                 475                 480
Ala Gly Pro Arg Phe Thr Gly Gly Asp Ile Ile Gln Cys Thr Glu Asn
                485                 490                 495
Gly Ser Ala Ala Thr Ile Tyr Val Thr Pro Asp Val Ser Tyr Ser Gln
            500                 505                 510
Lys Tyr Arg Ala Arg Ile His Tyr Ala Ser Thr Ser Gln Ile Thr Phe
        515                 520                 525
Thr Leu Ser Leu Asp Gly Ala Pro Phe Asn Gln Tyr Tyr Phe Asp Lys
        530                 535                 540
Thr Ile Asn Lys Gly Asp Thr Leu Thr Tyr Asn Ser Phe Asn Leu Ala
545                 550                 555                 560
Ser Phe Ser Thr Pro Phe Glu Leu Ser Gly Asn Asn Leu Gln Ile Gly
                565                 570                 575
```

```
Val Thr Gly Leu Ser Ala Gly Asp Lys Val Tyr Ile Asp Lys Ile Glu
            580                 585                 590

Phe Ile Pro Val Asn
        595

(2) INFORMATION FOR SEQ ID NO:3:

(i) SEQUENCE CHARACTERISTICS:
        (A) LENGTH: 1833 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ATGGCTGCAG ACAACAACAC GGAGGCCCTC GATAGCTCTA CCACCAAAGA TGTCATTCAG      60

AAGGGCATCT CCGTTGTGGG TGATCTCCTT GGCGTTGTTG GTTTCCCCTT TGGTGGTGCC     120

CTTGTTTCGT TCTACACTAA CTTTCTGAAT ACTATTTGGC CCAGCGAAGA CCCTTGGAAG     180

GCTTTTATGG AGCAAGTGGA AGCTTTGATG GATCAGAAGA TCGCTGATTA TGCAAAGAAC     240

AAAGCTCTTG CTGAGCTCCA GGGCCTTCAG AACAACGTCG AAGATTATGT GAGTGCACTG     300

AGTTCATGGC AAAAGAATCC TGTGTCCTCA CGAAATCCAC ATAGCCAGGG GCGCATAAGG     360

GAGCTGTTCT CTCAAGCAGA AAGTCACTTC CGGAATTCAA TGCCTTCCTT TGCCATCTCT     420

GGGTACGAGG TTCTCTTTCT TACAACCTAC GCTCAAGCTG CCAACACACA TCTGTTCTTA     480

CTAAAAGACG CTCAAATCTA TGGTGAAGAA TGGGGATACG AGAAAGAAGA TATCGCTGAG     540

TTCTACAAGC GTCAACTAAA ACTTACTCAA GAGTATACTG ACCACTGTGT CAAATGGTAT     600

AATGTTGGAT TGGATAAGTT GAGAGGTTCA TCTTATGAAT CTTGGGTAAA CTTTAACCGG     660

TACCGCAGAG AGATGACATT GACAGTGCTC GACTTGATTG CACTATTTCC ATTGTATGAT     720

GTTCGACTCT ACCCAAAGGA GGTTAAAACC GAATTGACTA GAGACGTTTT AACCGATCCC     780

ATTGTCGGAG TCAACAACCT CAGAGGCTAC GGAACAACCT TCTCTAACAT AGAAAACTAC     840

ATTCGTAAAC ACATCTATT CGACTATCTG CACAGAATTC AGTTTCACAC GCGGTTCCAA      900

CCAGGATACT ATGGAAATGA CTCTTTCAAC TATTGGTCCG GTAATTATGT TTCAACTAGA     960

CCCAGCATAG GATCTAATGA CATCATCACC TCTCCATTCT ACGGAAACAA GTCCTCCGAG    1020

CCTGTGCAAA ACTTGGAGTT TAATGGAGAG AAAGTCTATA GAGCCGTGGC CAATACCAAT    1080

CTTGCCGTCT GGCCGTCCGC TGTGTACTCA GGTGTTACCA AAGTGGAATT CAGCCAATAC    1140

AATGATCAGA CAGATGAAGC AAGTACTCAA ACTTACGACT CAAAGAGGAA TGTTGGCGCG    1200

GTCAGCTGGG ATTCTATCGA TCAACTCCCT CCAGAAACCA CCGATGAACC TCTAGAGAAG    1260

GGTTATAGCC ATCAACTCAA TTACGTAATG TGCTTTCTCA TGCAGGGTAG TAGAGGTACC    1320

ATCCCAGTGT TAACTTGGAC TCACAAGAGT GTAGACTTCT TCAACATGAT TGATTCGAAA    1380

AAGATTACTC AACTTCCGTT GGTAAAGGCC TACAAGTTAC AATCTGGTGC TTCCGTTGTC    1440

GCAGGTCCTA GGTTTACAGG AGGAGATATC ATTCAATGCA CTGAGAATGG GTCCGCGGCA    1500

ACTATCTACG TTACACCTGA TGTGTCGTAC TCTCAAAAGT ATCGTGCTAG AATTCATTAT    1560

GCTTCTACCT CTCAGATAAC ATTCACACTA AGCTTGGACG GGCTCCATT CAACCAATAC     1620

TACTTCGATA AGACCATCAA CAAAGGAGAC ACACTCACGT ATAATTCATT CAACTTAGCC    1680

AGCTTCAGCA CTCCATTCGA ATTGTCAGGG AACAACTTGC AGATAGGCGT CACAGGATTG    1740

AGTGCTGGTG ACAAGGTTTA CATCGACAAG ATTGAGTTCA TTCCAGTGAA CCTTAGGTCC    1800
```

CCAGGAACCG AGCTTGAGTT CATCGACATC TAG    1833

(2) INFORMATION FOR SEQ ID NO:4:

(i) SEQUENCE CHARACTERISTICS:
        (A) LENGTH: 610 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ala Ala Asp Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
            35                  40                  45

Leu Asn Thr Ile Trp Pro Ser Glu Asp Pro Trp Lys Ala Phe Met Glu
50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Val Ser Ser Arg Asn
            100                 105                 110

Pro His Ser Gln Gly Arg Ile Arg Glu Leu Phe Ser Gln Ala Glu Ser
            115                 120                 125

His Phe Arg Asn Ser Met Pro Ser Phe Ala Ile Ser Gly Tyr Glu Val
            130                 135                 140

Leu Phe Leu Thr Thr Tyr Ala Gln Ala Ala Asn Thr His Leu Phe Leu
145                 150                 155                 160

Leu Lys Asp Ala Gln Ile Tyr Gly Glu Glu Trp Gly Tyr Glu Lys Glu
                165                 170                 175

Asp Ile Ala Glu Phe Tyr Lys Arg Gln Leu Lys Leu Thr Gln Glu Tyr
            180                 185                 190

Thr Asp His Cys Val Lys Trp Tyr Asn Val Gly Leu Asp Lys Leu Arg
            195                 200                 205

Gly Ser Ser Tyr Glu Ser Trp Val Asn Phe Asn Arg Tyr Arg Arg Glu
            210                 215                 220

Met Thr Leu Thr Val Leu Asp Leu Ile Ala Leu Phe Pro Leu Tyr Asp
225                 230                 235                 240

Val Arg Leu Tyr Pro Lys Glu Val Lys Thr Glu Leu Thr Arg Asp Val
                245                 250                 255

Leu Thr Asp Pro Ile Val Gly Val Asn Asn Leu Arg Gly Tyr Gly Thr
            260                 265                 270

Thr Phe Ser Asn Ile Glu Asn Tyr Ile Arg Lys Pro His Leu Phe Asp
            275                 280                 285

Tyr Leu His Arg Ile Gln Phe His Thr Arg Phe Gln Pro Gly Tyr Tyr
            290                 295                 300

Gly Asn Asp Ser Phe Asn Tyr Trp Ser Gly Asn Tyr Val Ser Thr Arg
305                 310                 315                 320

Pro Ser Ile Gly Ser Asn Asp Ile Ile Thr Ser Pro Phe Tyr Gly Asn
                325                 330                 335
```

Lys Ser Ser Glu Pro Val Gln Asn Leu Glu Phe Asn Gly Glu Lys Val
              340                 345                 350

Tyr Arg Ala Val Ala Asn Thr Asn Leu Ala Val Trp Pro Ser Ala Val
          355                 360                 365

Tyr Ser Gly Val Thr Lys Val Glu Phe Ser Gln Tyr Asn Asp Gln Thr
    370                 375                 380

Asp Glu Ala Ser Thr Gln Thr Tyr Asp Ser Lys Arg Asn Val Gly Ala
385                 390                 395                 400

Val Ser Trp Asp Ser Ile Asp Gln Leu Pro Pro Glu Thr Thr Asp Glu
                405                 410                 415

Pro Leu Glu Lys Gly Tyr Ser His Gln Leu Asn Tyr Val Met Cys Phe
                420                 425                 430

Leu Met Gln Gly Ser Arg Gly Thr Ile Pro Val Leu Thr Trp Thr His
            435                 440                 445

Lys Ser Val Asp Phe Phe Asn Met Ile Asp Ser Lys Lys Ile Thr Gln
        450                 455                 460

Leu Pro Leu Val Lys Ala Tyr Lys Leu Gln Ser Gly Ala Ser Val Val
465                 470                 475                 480

Ala Gly Pro Arg Phe Thr Gly Gly Asp Ile Ile Gln Cys Thr Glu Asn
                485                 490                 495

Gly Ser Ala Ala Thr Ile Tyr Val Thr Pro Asp Val Ser Tyr Ser Gln
                500                 505                 510

Lys Tyr Arg Ala Arg Ile His Tyr Ala Ser Thr Ser Gln Ile Thr Phe
            515                 520                 525

Thr Leu Ser Leu Asp Gly Ala Pro Phe Asn Gln Tyr Tyr Phe Asp Lys
        530                 535                 540

Thr Ile Asn Lys Gly Asp Thr Leu Thr Tyr Asn Ser Phe Asn Leu Ala
545                 550                 555                 560

Ser Phe Ser Thr Pro Phe Glu Leu Ser Gly Asn Asn Leu Gln Ile Gly
                565                 570                 575

Val Thr Gly Leu Ser Ala Gly Asp Lys Val Tyr Ile Asp Lys Ile Glu
            580                 585                 590

Phe Ile Pro Val Asn Leu Arg Ser Pro Gly Thr Glu Leu Glu Phe Ile
        595                 600                 605

Asp Ile
    610

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

CAGGATCCAA CAATGAC                                                          17

(2) INFORMATION FOR SEQ ID NO:6:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AAGGTAAGT                                                                                      9

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TTTTUTTTUT UTUTUTGCAG C                                                                        21

(2) INFORMATION FOR SEQ ID NO:8:

(i) SEQUENCE CHARACTERISTICS:
        (A) LENGTH: 456 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AATTGGGATC CAACAATGGC TGCAGACAAC AACACGGAGG CCCTCGATAG CTCTACCACC         60

CCCTAGGTTG TTACCGACGT CTGTTGTTGT GCCTCCGGGA GCTATCGAGA TGGTGGAAAG        120

ATGTCATTCA GAAGGGCATC TCCGTTGTGG GTGATCTCCT TGGCGTTGTT GGTTTCTTTC        180

TACAGTAAGT CTTCCCGTAG AGGCAACACC CACTAGAGGA ACCGCAACAA CCAAAGCCCT        240

TTGGTGGTGC CCTTGTTTCG TTCTACACTA ACTTTCTGAA TACTATTTGG CCCAGCGGGA        300

AACCACCACG GGAACAAAGC AAGATGTGAT TGAAAGACTT ATGATAAACC GGGTCGGAAG        360

ACCCTTGGAA GGCTTTTATG GAGCAAGTGG AAGCTTAGAT CTAGCTTCTG GGAACCTTCC        420

GAAAATACCT CGTTCACCTT CGAATCTAGA TCTTAA                                 456

(2) INFORMATION FOR SEQ ID NO:9:

(i) SEQUENCE CHARACTERISTICS:
        (A) LENGTH: 504 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

AATTAAGCTT GGACGGGGCT CCATTCAACC AATACTACTT CGATAAGACC ATCAACAAAG         60

TTCGAACCTG CCCCGAGGTA AGTTGGTTAT GATGAAGCTA TTCTGGTAGT TGTTTCGAGA        120

CACACTCACG TATAATTCCT TCAACTTAGC CAGCTTCAGC ACTCCATTCG AATTGTCTCT        180

GTGTGAGTGC ATATTAAGGA AGTTGAATCG GTCGAAGTCG TGAGGTAAGC TTAACACAGG        240

GAACAACTTG CAGATAGGCG TCACAGGATT GAGTGCTGGT GACAAGGTCT ACATCGGTCC        300

CTTGTTGAAC GTCTATCCGC AGTGTCCTAA CTCACGACCA CTGTTCCAGA TGTAGCACAA        360

GATTGAGTTC ATTCCAGTGA ACCTTAGGTC CCCAGGAACC GAGCTTGAGT TCATCGTGTT        420

CTAACTCAAG TAAGGTCACT TGGAATCCAG GGGTCCTTGG CTCGAACTCA AGTAGCACAT        480

CTAGATCTTG TAGATCTAGA TTAA                                              504